(12) United States Patent
Prygoski et al.

(10) Patent No.: US 8,012,155 B2
(45) Date of Patent: Sep. 6, 2011

(54) APPARATUS AND METHOD FOR PROPHYLACTIC HIP FIXATION

(75) Inventors: Matthew P. Prygoski, Okemos, MI (US); Antony J. Lozier, Warsaw, IN (US); Russell M. Parrott, Warsaw, IN (US); Andrew L. Gray, Warren, IN (US); Nicolas J. Pacelli, Cedar Park, TX (US)

(73) Assignee: Zimmer, Inc., Warsaw, IN (US)

( * ) Notice: Subject to any disclaimer, the term of this patent is extended or adjusted under 35 U.S.C. 154(b) by 327 days.

(21) Appl. No.: 12/417,076

(22) Filed: Apr. 2, 2009

(65) Prior Publication Data
US 2010/0256640 A1    Oct. 7, 2010

(51) Int. Cl.
*A61B 17/56* (2006.01)

(52) U.S. Cl. .............................. 606/62; 606/65; 606/280

(58) Field of Classification Search ............... 606/62–68, 606/280, 282, 286, 300, 301, 323, 329
See application file for complete search history.

(56) References Cited

U.S. PATENT DOCUMENTS

| | | |
|---|---|---|
| 2,381,050 A | 8/1945 | Hardinge |
| 2,490,364 A | 12/1949 | Livingston |
| 2,699,774 A | 1/1955 | Livingston |
| 3,716,051 A | 2/1973 | Fischer |
| 3,846,846 A | 11/1974 | Fischer |
| 4,169,470 A | 10/1979 | Ender et al. |
| 4,236,512 A | 12/1980 | Aginsky |
| 4,379,451 A | 4/1983 | Getscher |
| 4,409,974 A | 10/1983 | Freedland |
| 4,453,539 A | 6/1984 | Raftopoulos et al. |
| 4,483,335 A | 11/1984 | Tornier |
| 4,590,930 A | 5/1986 | Kurth et al. |
| 4,632,101 A | 12/1986 | Freedland |
| 4,712,541 A | 12/1987 | Harder et al. |
| 4,760,843 A | 8/1988 | Fischer et al. |
| 4,781,181 A | 11/1988 | Tanguy |
| 4,854,312 A | 8/1989 | Raftopoulos et al. |
| 4,969,887 A | 11/1990 | Sodhi |
| 5,013,314 A | 5/1991 | Firica et al. |

(Continued)

FOREIGN PATENT DOCUMENTS

EP    2074956 A1    7/2009

(Continued)

OTHER PUBLICATIONS

Website: www.orthosupersite.com, accessed Jan. 11, 2011.

*Primary Examiner* — Eduardo C Robert
*Assistant Examiner* — Atiya Mahmud
(74) *Attorney, Agent, or Firm* — Baker & Daniels LLP

(57) ABSTRACT

A method and apparatus configured to strengthen and support a portion of a bone, such as the femoral head of the proximal femur, for example. The apparatus may include a housing or base member and a movable support member connected to the housing and configured to move between a first, undeployed position in which the support member is disposed proximate the housing or base such that the apparatus may be inserted into bone, and a second, deployed position in which the support member extends away from the housing or base for supporting the femoral head. The support member may be a rod, one or more wires, a leaf spring, a bladder, or an expandable mesh material, for example.

18 Claims, 24 Drawing Sheets

U.S. PATENT DOCUMENTS

| | | | |
|---|---|---|---|
| 5,057,103 A | 10/1991 | Davis | |
| 5,116,335 A | 5/1992 | Hannon et al. | |
| 5,441,500 A | 8/1995 | Seidel et al. | |
| 5,578,035 A | 11/1996 | Lin | |
| 5,759,184 A | 6/1998 | Santangelo | |
| 5,810,820 A | 9/1998 | Santori et al. | |
| 5,827,289 A | 10/1998 | Reiley et al. | |
| 5,919,194 A | 7/1999 | Anderson | |
| 5,971,986 A | 10/1999 | Santori et al. | |
| 5,972,015 A | 10/1999 | Scribner et al. | |
| 6,066,154 A | 5/2000 | Reiley et al. | |
| 6,126,691 A | 10/2000 | Kasra et al. | |
| 6,200,317 B1 | 3/2001 | Aalsma et al. | |
| 6,224,600 B1 | 5/2001 | Protogirou | |
| 6,235,043 B1 | 5/2001 | Reiley et al. | |
| 6,248,110 B1 | 6/2001 | Reiley et al. | |
| 6,261,289 B1 | 7/2001 | Levy | |
| 6,355,069 B1 | 3/2002 | DeCarlo, Jr. et al. | |
| 6,447,514 B1 | 9/2002 | Stalcup et al. | |
| 6,454,810 B1 | 9/2002 | Lob | |
| 6,508,841 B2 | 1/2003 | Martin et al. | |
| 6,551,321 B1 | 4/2003 | Burkinshaw et al. | |
| 6,554,833 B2 | 4/2003 | Levy et al. | |
| 6,575,973 B1 * | 6/2003 | Shekalim | 606/62 |
| 6,613,052 B1 | 9/2003 | Kinnett | |
| 6,648,889 B2 | 11/2003 | Bramlet et al. | |
| 6,679,890 B2 * | 1/2004 | Margulies et al. | 606/94 |
| 6,719,793 B2 | 4/2004 | McGee | |
| 6,736,818 B2 | 5/2004 | Perren et al. | |
| 6,767,350 B1 | 7/2004 | Lob | |
| 6,780,185 B2 | 8/2004 | Frei et al. | |
| 6,783,530 B1 | 8/2004 | Levy | |
| 6,942,668 B2 | 9/2005 | Padget et al. | |
| 7,052,498 B2 * | 5/2006 | Levy et al. | 606/63 |
| 7,097,648 B1 | 8/2006 | Globerman et al. | |
| 7,241,303 B2 | 7/2007 | Reiss et al. | |
| 7,261,720 B2 | 8/2007 | Stevens et al. | |
| 7,507,241 B2 | 3/2009 | Levy et al. | |
| 7,601,152 B2 | 10/2009 | Levy et al. | |
| 2003/0220644 A1 | 11/2003 | Thelen et al. | |
| 2004/0049192 A1 | 3/2004 | Shimizu | |
| 2005/0065526 A1 | 3/2005 | Drew et al. | |
| 2005/0143827 A1 | 6/2005 | Globerman et al. | |
| 2005/0159749 A1 * | 7/2005 | Levy et al. | 606/72 |
| 2006/0084998 A1 | 4/2006 | Levy et al. | |
| 2006/0122601 A1 | 6/2006 | Tandon | |
| 2006/0229617 A1 | 10/2006 | Meller et al. | |
| 2006/0264943 A1 | 11/2006 | Chieng | |
| 2006/0264951 A1 | 11/2006 | Nelson et al. | |
| 2007/0250062 A1 | 10/2007 | Ara Pinilla et al. | |
| 2007/0282443 A1 | 12/2007 | Globerman et al. | |
| 2008/0188897 A1 | 8/2008 | Krebs et al. | |
| 2008/0221575 A1 | 9/2008 | Betts | |
| 2008/0262495 A1 | 10/2008 | Coati et al. | |
| 2008/0269746 A1 | 10/2008 | Justin | |
| 2008/0269748 A1 | 10/2008 | Justin et al. | |
| 2009/0005782 A1 | 1/2009 | Chirico et al. | |
| 2009/0125028 A1 | 5/2009 | Teisen et al. | |
| 2009/0182336 A1 | 7/2009 | Brenzel et al. | |
| 2010/0023012 A1 | 1/2010 | Voor | |

FOREIGN PATENT DOCUMENTS

| | | |
|---|---|---|
| WO | WO97/18769 A1 | 5/1997 |
| WO | WO98/51228 A1 | 11/1998 |
| WO | WO03/007830 A1 | 1/2003 |
| WO | WO2007/134248 A1 | 11/2007 |
| WO | WO2009037471 A2 | 3/2009 |
| WO | WO2009/150691 A1 | 12/2009 |

* cited by examiner

APPARATUS AND METHOD FOR PROPHYLACTIC HIP FIXATION

BACKGROUND

1. Field of the Invention

The present invention relates to an apparatus and method for supporting and/or stabilizing a bone structure, such as the femoral head of the proximal femur.

2. Description of the Related Art

In general, known techniques for treating weakened bone structure in the proximal femur involve the use of intramedullary nails or bone plates and bone screws configured to provide a mechanism for stabilizing the bone. These devices are typically utilized after the bone has fractured in order to facilitate the healing of the fracture. Thus, these types of components are helpful in healing a damaged bone but may not generally prevent the bone from initially fracturing.

The replacement of damaged or weakened hips is also known. For example, U.S. Pat. No. 7,044,978 is hereby incorporated herein in its entirety by reference and discloses a positioner and method for a femoral hip implant. The disclosed hip implant is configured to replace a damaged or weakened bone. The hip implant is generally inserted into the intramedullary canal of a femur and replaces the femoral head of the bone. The replacement implant may be inserted into a pelvis comprising natural bone or including a replacement component. Accordingly, the replacement implant takes the place of the natural femoral head and a portion of the femur.

SUMMARY

The present invention provides a method and apparatus configured to strengthen and support a portion of a bone, such as the femoral head of the proximal femur, for example. The apparatus may include a housing or base member and a movable support member connected to the housing and configured to move between a first, undeployed position in which the support member is disposed proximate the housing or base such that the apparatus may be inserted into bone, and a second, deployed position in which the support member extends away from the housing or base for supporting the femoral head. The support member may be a rod, one or more wires, a leaf spring, a bladder, or an expandable mesh material, for example.

In one embodiment, the apparatus further includes a means for controlling the position of the support member, such as a cable. The cable may be connected to the support member and may at least partially extend through the housing. The housing may include an opening, and the support member may be located within the housing in the first position. In the second position, the support member may at least partially extend through the opening. The housing may include a second opening, and the cable may at least partially extend through the second opening. In one embodiment, the support member includes an inclined surface and a pair of extensions, and the housing includes a pair of slots configured to receive the extensions. The housing may include an inclined surface configured to engage the inclined surface of the member as the support member moves from the first position to the second position. In addition, the cable may be connected to the member proximate the extensions.

In another embodiment, the support member may comprise a leaf spring, and in other embodiments the support member may comprise a wire. The wire may include a proximal end and a distal end. The proximal end may be fixed with respect to the housing, and the distal end of the wire may be fixed with respect to the housing.

In another embodiment, the support member includes at least two wires. Each wire may include a proximal end and a distal end. The distal ends of the wires may be connected to the housing.

A further embodiment of the invention includes an apparatus including means for providing support to the femoral head by extending into the femoral head. The apparatus may include means for moving the support means from a first configuration and a second configuration. The first configuration may allow the support means to pass through an opening in the bone, and the second configuration may cause the support means to extend into the femoral head.

Advantageously, the embodiments of the present invention may be used prophylactically by being inserted within the proximal femur prior to a fracture of the femoral neck and/or other severe damage of the proximal femur. In this manner, use of the present invention may provide rigidity and strength to the proximal femur. As a result, fracture of the femoral neck and/or other severe damage to the proximal femur may be prevented. For example, if a patient has suffered a fractured femoral neck on the left side of the patient's body, the present invention may be used prophylactically on the right side of the patient's body to prevent and/or lessen the potential for the femoral neck on the right side of the patient's body from suffering a similar fracture. Additionally, the present invention may be used in an individual diagnosed as being at high risk of suffering a femoral fracture, such as an individual diagnosed with osteoporosis.

In one form thereof, the present invention provides an apparatus configured to strengthen and support a portion of a bone, the apparatus including a housing; and a support member configured to move between a first, undeployed position in which the support member is disposed proximate the housing and a second, deployed position in which the support member is extended from the housing; and an actuator coupling the support member to the housing, the actuator configured to move the support member between the first and second positions.

In another form thereof, the present invention provides an apparatus configured to provide support to the femoral head of the proximal femur, the apparatus including means for providing support to the femoral head by extension into the femoral head; and means for moving the support means from a first configuration and a second configuration, wherein the first configuration allows the support means to pass through an opening in the bone and the second configuration causes the support means to extend into the femoral head.

In yet another form thereof, the present invention provides a method for the prophylactic treatment of a proximal femur, the method including the steps of identifying a fracture in one of a medial proximal femur and a lateral proximal femur, and implanting an apparatus in the other of the medial proximal femur and the lateral proximal femur to support and strengthen the other of the medial proximal femur and the lateral proximal femur prior to a fracture developing in the other of the medial proximal femur and the lateral proximal femur.

In yet another form thereof, the present invention provides a method of prophylactic treatment of a proximal femur, the method including the steps of identifying that a patient has one of a disease and an aliment that increases the likelihood of the patient experiencing a fracture of one of a medial proximal femur and a lateral proximal femur and implanting an apparatus in at least one of the medial proximal femur and the lateral proximal femur to strength and support the at least one of the medial proximal femur and the lateral proximal femur prior to a fracture developing in the at least one of the medial proximal femur and the lateral proximal femur.

BRIEF DESCRIPTION OF THE DRAWINGS

The above-mentioned and other features of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

Figure 1:
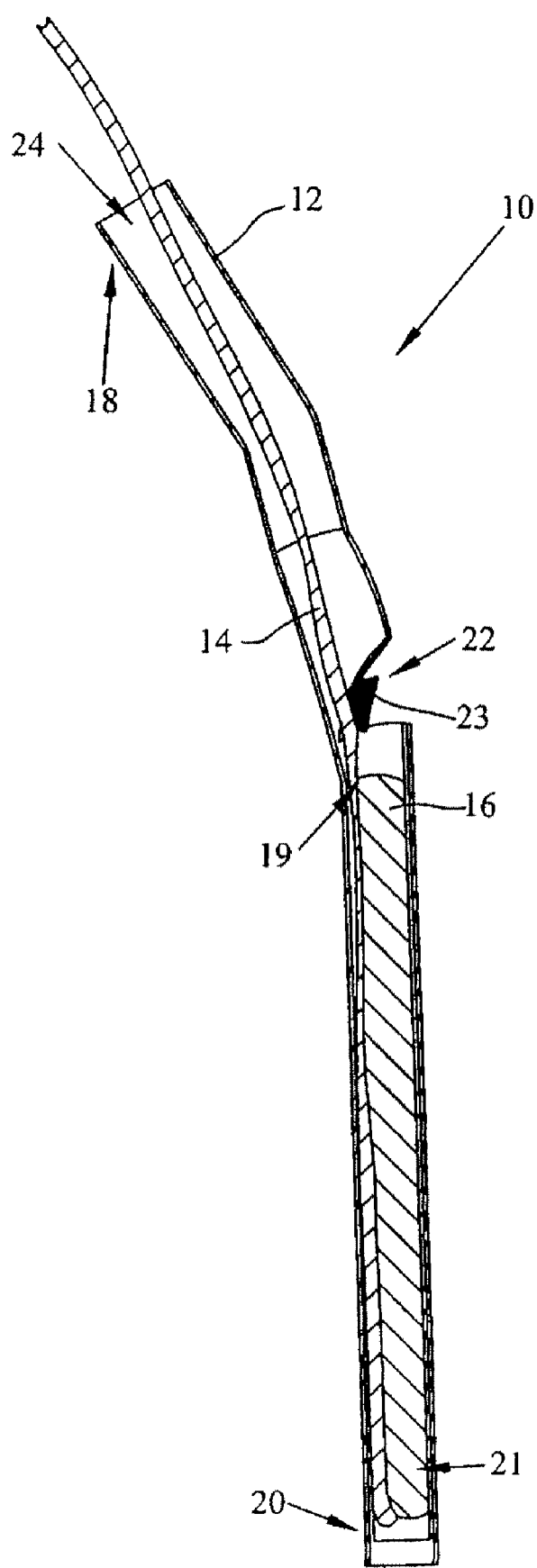
FIG. 1 is a sectional view of one embodiment of a support apparatus.
Figure 2B:
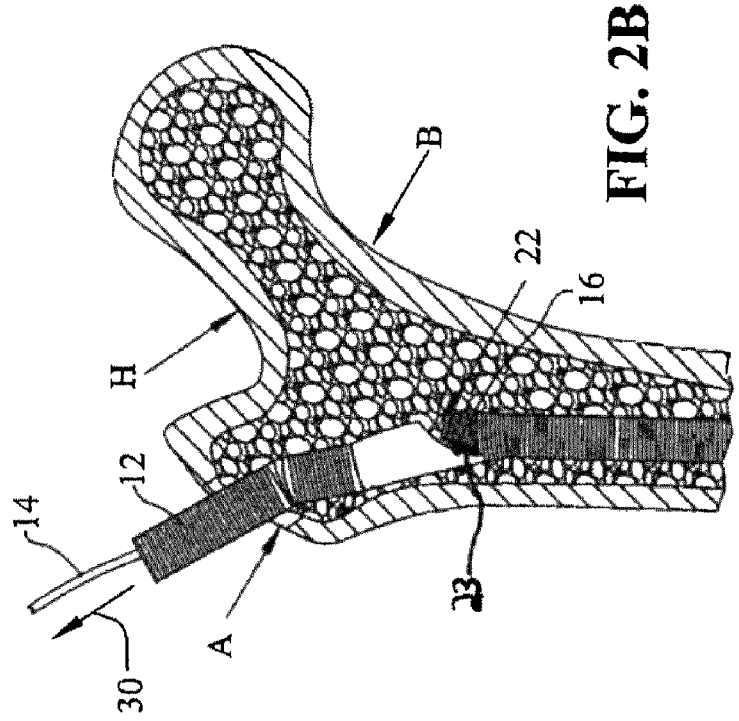
FIGS. 2A-2D are sequential views showing the insertion and deployment into a bone of the support apparatus of FIG. 1.
Figure 2A:
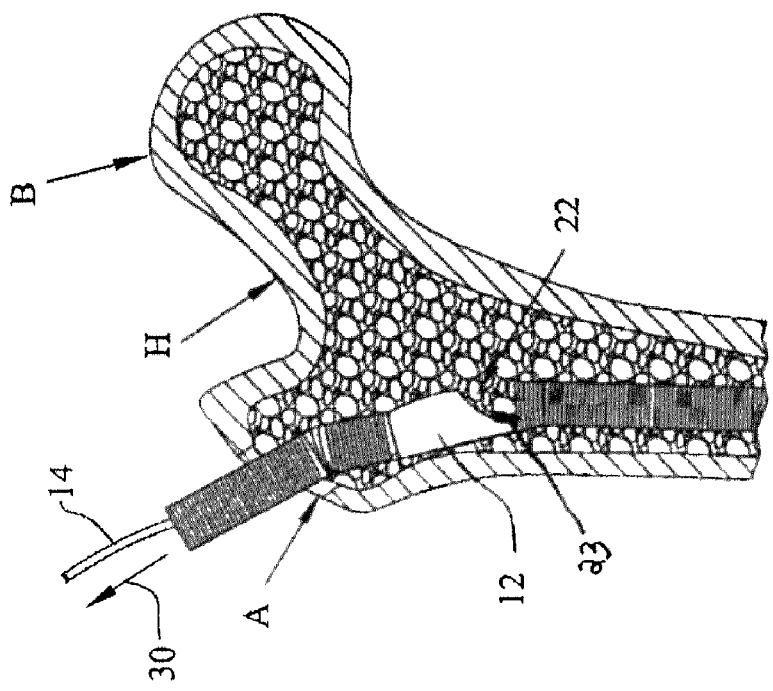
Figure 2C:
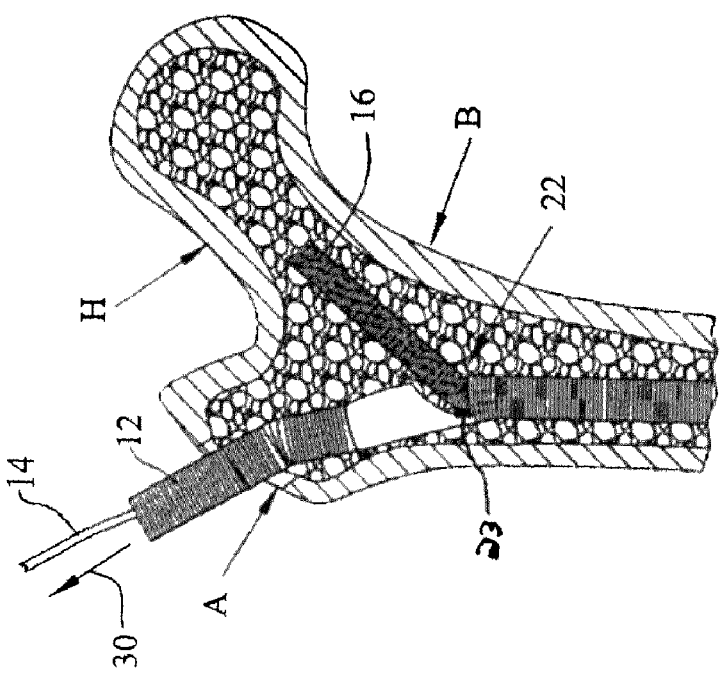
Figure 2D:
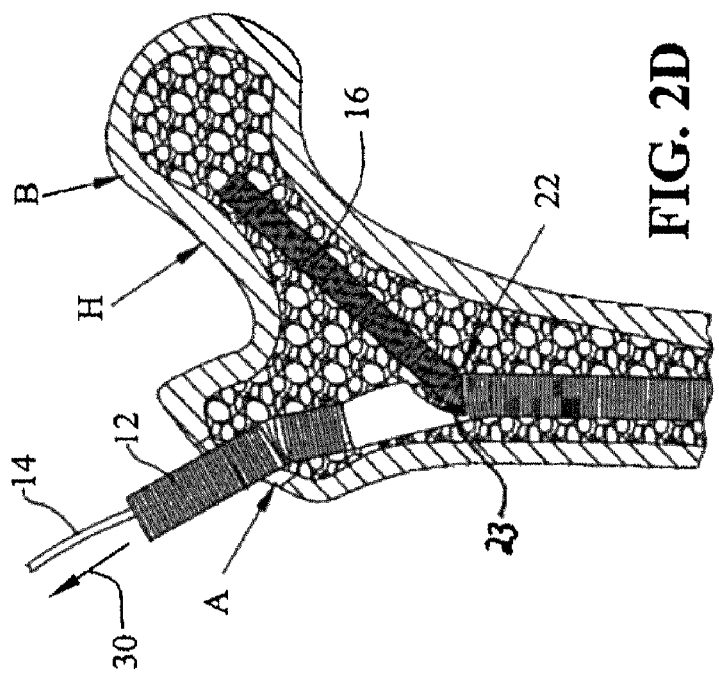

FIG. 1 is a sectional view of an apparatus representing an embodiment of the present invention, generally indicated by numeral 10. Apparatus 10 includes a housing 12, a cable 14 and a support member 16. In the depicted embodiment, housing 12 has a substantially circular cross section and includes a proximal end 18 and a distal end 20. Housing 12 is substantially hollow and includes an opening 22 formed in the side of the housing 12. Housing 12 also includes an opening 24 formed in the proximal end 18.

Support member 16 includes a proximal end 19 and a distal end 21. The cable 14 is connected to the support member 16 in a manner ensuring that the movement of cable 14 translates into movement of the support member 16. For example, the cable 14 may be connected to the support member 16 at least near the distal end 21 of the support member 16.

In the depicted embodiment, the support member 16 is at least partially flexible. In addition, the support member 16 is sized so that the proximal end 19 of the support member 16 may extend outward from the opening 22.

With reference now to FIGS. 2A through 2D, apparatus 10 may be inserted into a bone B in order to strengthen bone B. In the depicted example, bone B is the proximal femur, and apparatus 10 is intended to strengthen at least the portion of bone B including the femoral head and neck H. Apparatus 10 is inserted into an aperture A formed in the greater trochanter of the proximal femur by a drill or other suitable device, for example. The aperture A is generally positioned within bone B to allow the apparatus 10 to be inserted into the intramedullary canal (partially shown) of the bone B. The apparatus 10 may be inserted into the intramedullary canal in any suitable manner.

Once the support apparatus 10 has been inserted into the canal, the surgeon may withdraw the cable 14 from the housing 12 in the direction of arrow 30. As explained above the movement of the cable 14 also results in movement of the support member 16. Housing 12 is configured so that as support member 16 is moved by cable 14, support member 16 exits housing 12 through the opening 22. For example, housing 12 may include a deflector plate 23 configured to direct support member 16 through the opening 22. As the cable 14 is pulled in the direction of arrow 30, the support member 16 will continue to pass through opening 22. In the depicted example, the support member 16 moves into the area of the femoral head and neck H. In general, the presence of the support member 16 within the femoral head and neck H will increase the strength of and provide support to the femoral head and neck H.

It should be noted that the apparatus 10 may be inserted into bone B prior to a fracture of the bone B. For example, apparatus 10 may be inserted into a bone B in an individual diagnosed as being at high risk of possibly having a bone B fracture, such as an individual having osteoporosis, or an individual who has suffered a similar fracture in another, similar bone. By inserting apparatus 10 into bone B, as described in detail above, apparatus 10 provides rigidity and strength to bone B. As a result, the likelihood of a subsequent fracture and/or other severe damage to bone B is substantially lessened. While the prophylactic use of the apparatus of the present invention is described herein with specific reference to apparatus 10, it is contemplated that the additional embodiments of the present invention may be used prophylactically in a substantially similar manner as described herein with reference to apparatus 10.

Support member 16 may be manufactured from any suitable biocompatible material. Embodiments of support member 16 may be formed from nitinol. For example, the support member 16 could be heat set at the curve depicted in FIG. 2D, prior to being pulled straight back into the housing 12, as shown in FIG. 1. Accordingly, upon deployment, the support member 16 would take the path of the femoral neck and extend into the femoral head.

Figure 3:
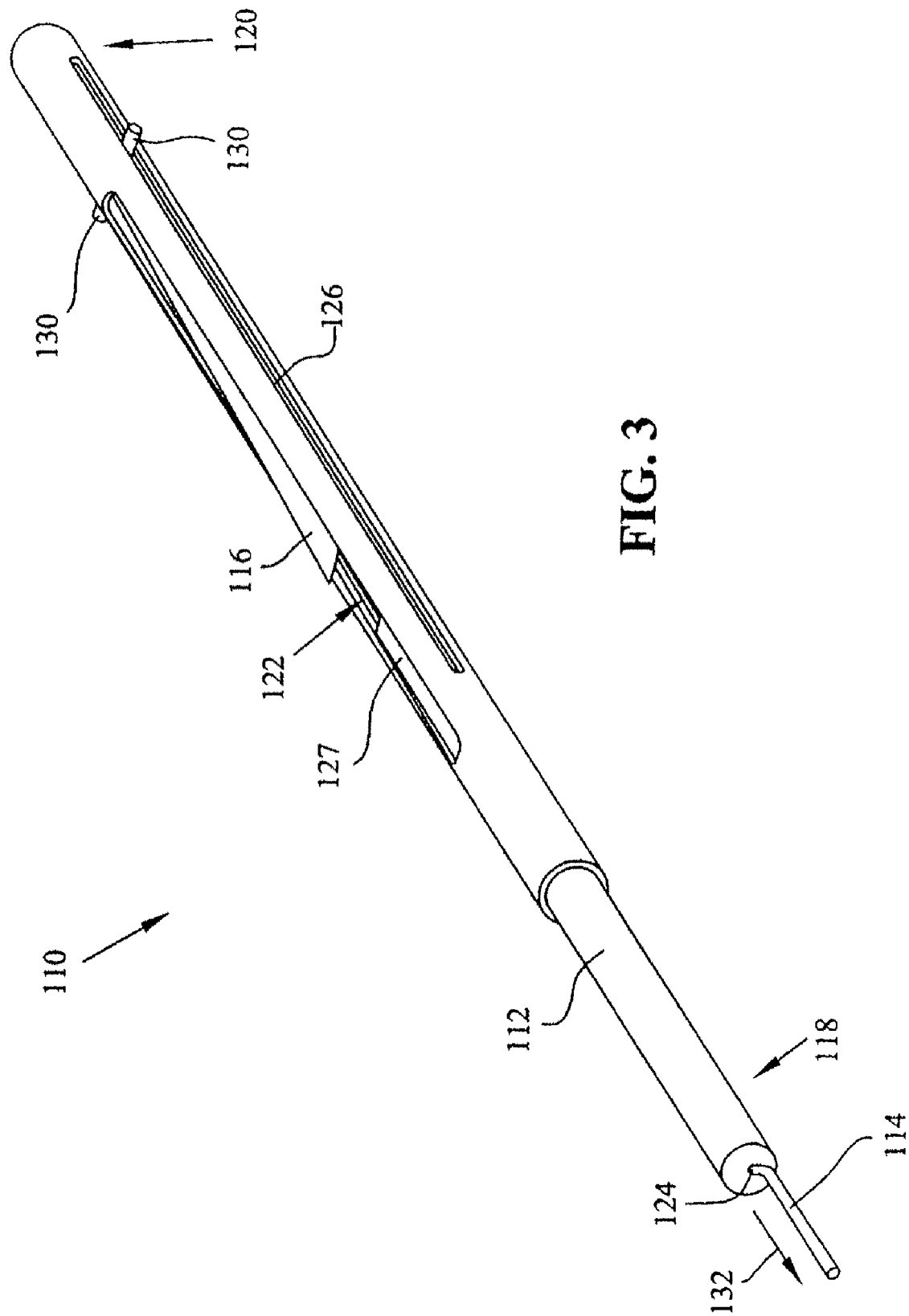
FIGS. 3 and 4 are perspective views of another embodiment of a support apparatus.
Figure 4:
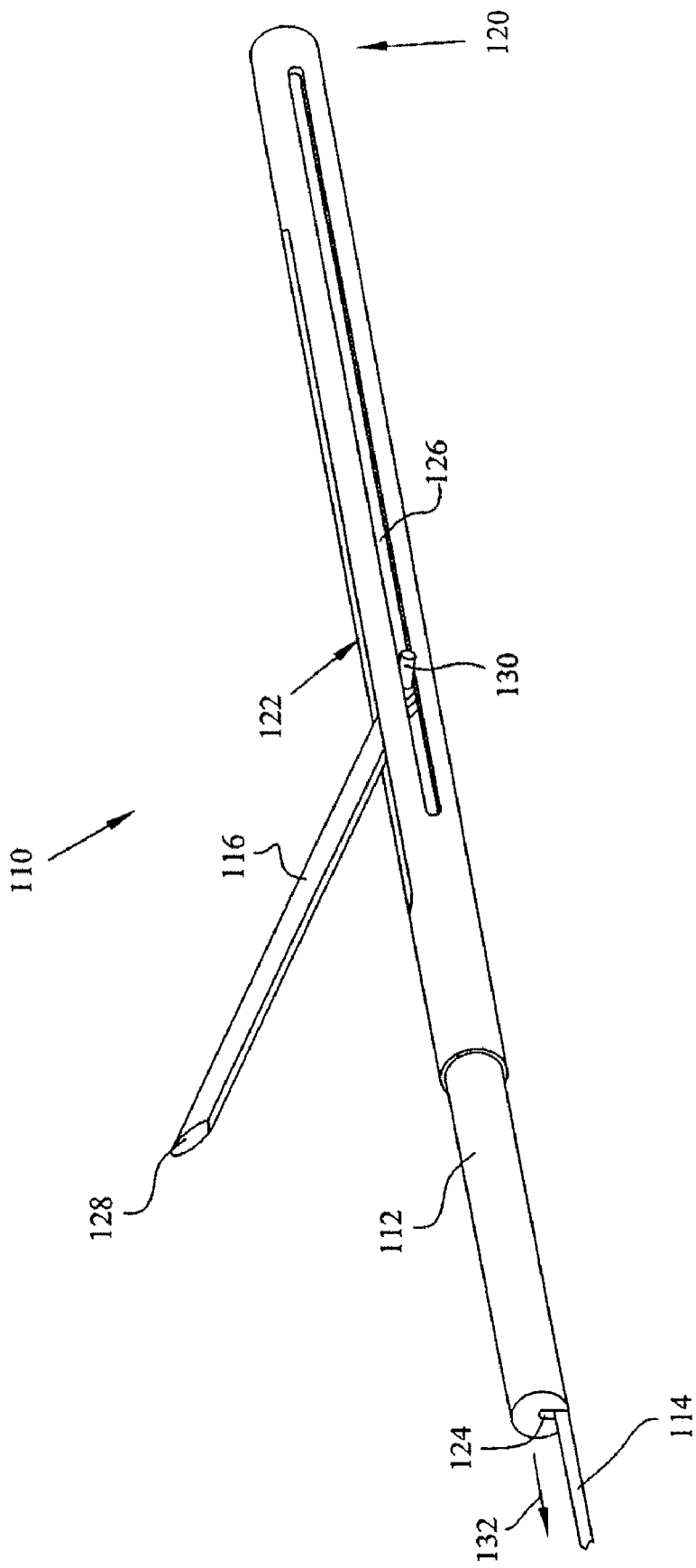

FIGS. 3 and 4 depict another embodiment of the support apparatus, generally indicated by numeral 110. In the depicted embodiment, apparatus 110 includes a housing 112 a cable 114 and a support member 116. Housing 112 includes a proximal end 118 and a distal end 120. In addition, housing 112 further includes an opening 122 formed in the top side of the housing 112, an opening 124 formed at the proximal end 118 and slots 126 formed in the sides of the housing 112. In the depicted embodiment, housing 112 includes an inclined member 127 retained in a relatively fixed position with respect to the remainder of the housing 112. In the depicted embodiment, inclined member 127 includes an inclined or ramped portion orientated along the longitudinal axis of support member 116.

Referring still to FIGS. 3 and 4, the support member 116 includes an inclined surface 128 and a pair of pegs 130. Cable 114 is connected to support member 116 proximate the pegs 130. Inclined surface 128 is sized and configured to engage the support member 116 in a manner forcing inclined surface 128 and support member 116 out of opening 122 of housing 112 as the inclined surface 128 moves across inclined member 127. Pegs 130 are sized and configured to be retained within slots 126.

In the depicted embodiment, movement of the cable 114 in the direction of arrow 132 will translate support member 116 in the direction of arrow 132. When inclined surface 128 contacts inclined member 127, support member 116 will also begin to extend outward from opening 122, and support member 116 will also begin to pivot about pegs 130. As the cable 114 continues to move in the direction of arrow 132, support member 116 will continue to pivot about pegs 130 until the portion of the support member 116 proximate the pegs 130 contacts inclined member 127. Inclined member 127 is configured to maintain support member 116 at an angle with respect to the housing 112. Accordingly, movement of cable 114 will cause the support member 116 to move between a first position, depicted in FIG. 3, and a second position, depicted in FIG. 4.

Figure 5:
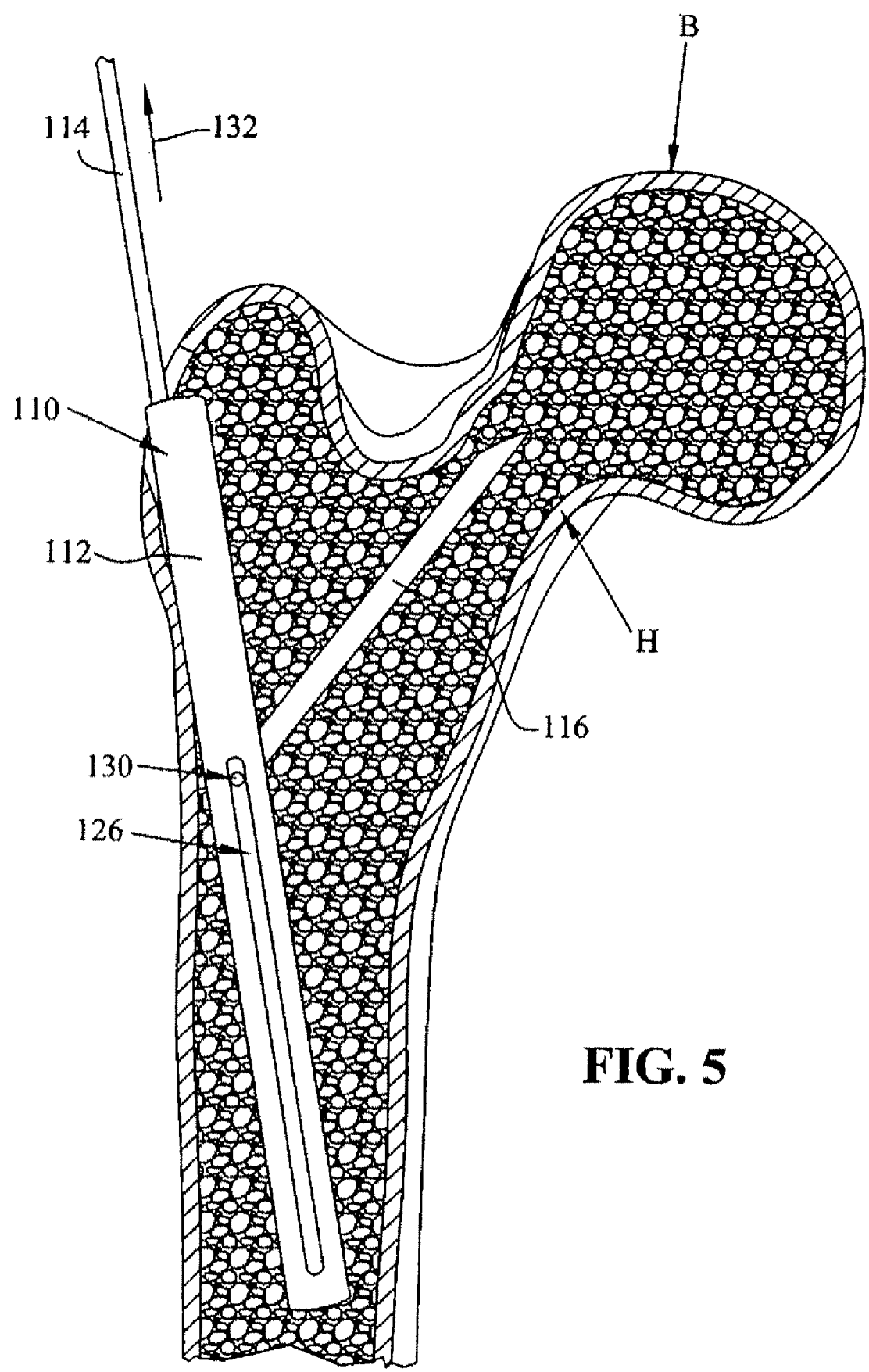
FIG. 5 is a sectional view of the support apparatus of FIGS. 3 and 4 inserted into a bone.

Accordingly, as shown in FIG. 5, apparatus 110 may be inserted into an aperture A formed in bone B when the support member 116 is located substantially within housing 112. In the depicted example, a drill (not shown) may form aperture A in the greater trochanter of the proximal femur including a femoral head and neck H. Once the apparatus 110 has been inserted into the bone B, a surgeon may then withdraw cable 114 from bone B in the direction of arrow 132. As explained above, the movement of the cable 114 in the direction of arrow 132 will cause the support member 116 to extend away from housing 112 and move into the position depicted in FIG. 5. Once the support member 116 is fully extended, as shown in FIG. 5, the support member 116 provides support to and strengthens the femoral head and neck H.

Figures 6A, 6B:
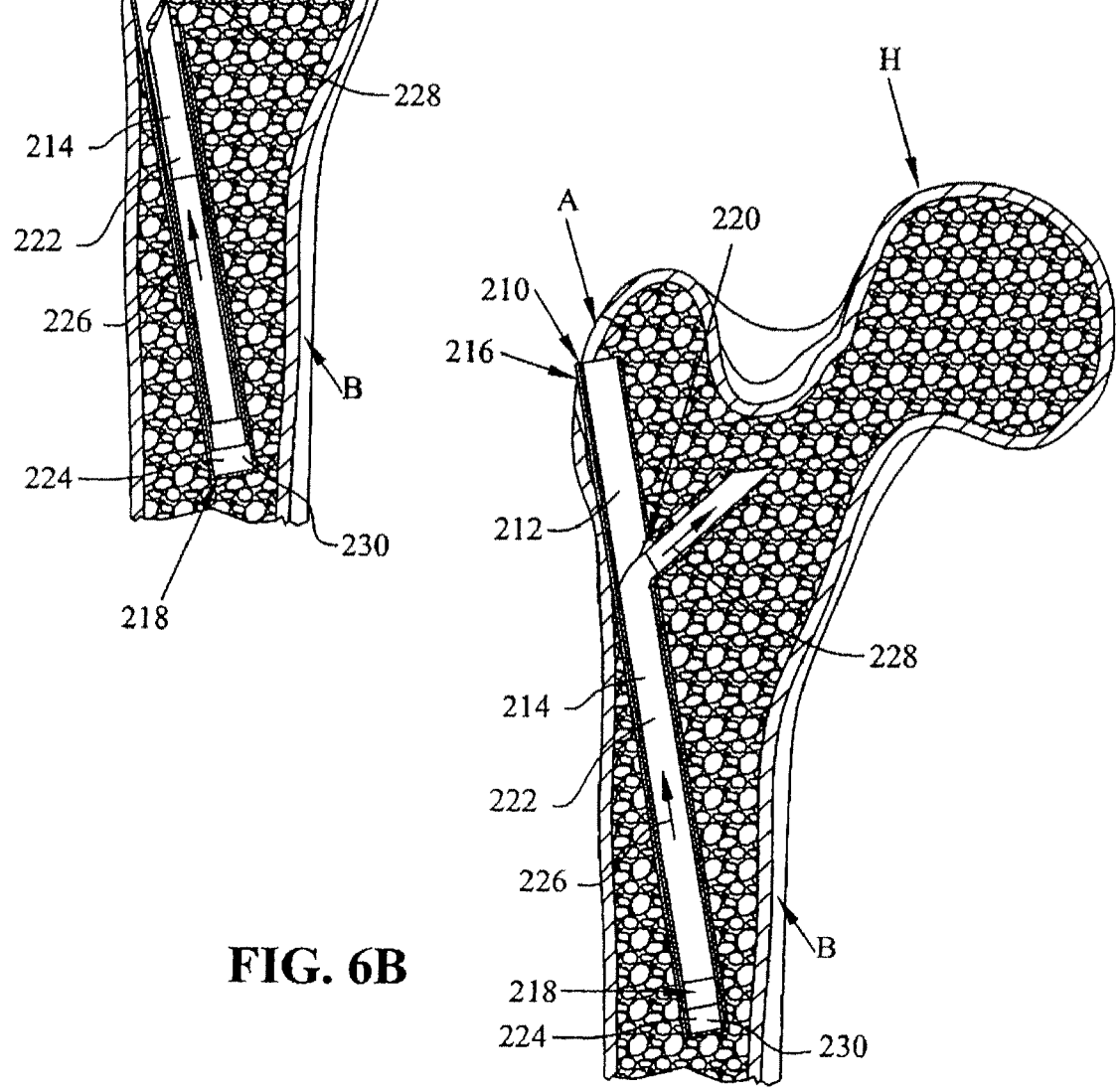
FIGS. 6A-6C are sequential views showing the insertion and deployment into a bone of the support apparatus of FIG. 5.
Figure 6C:
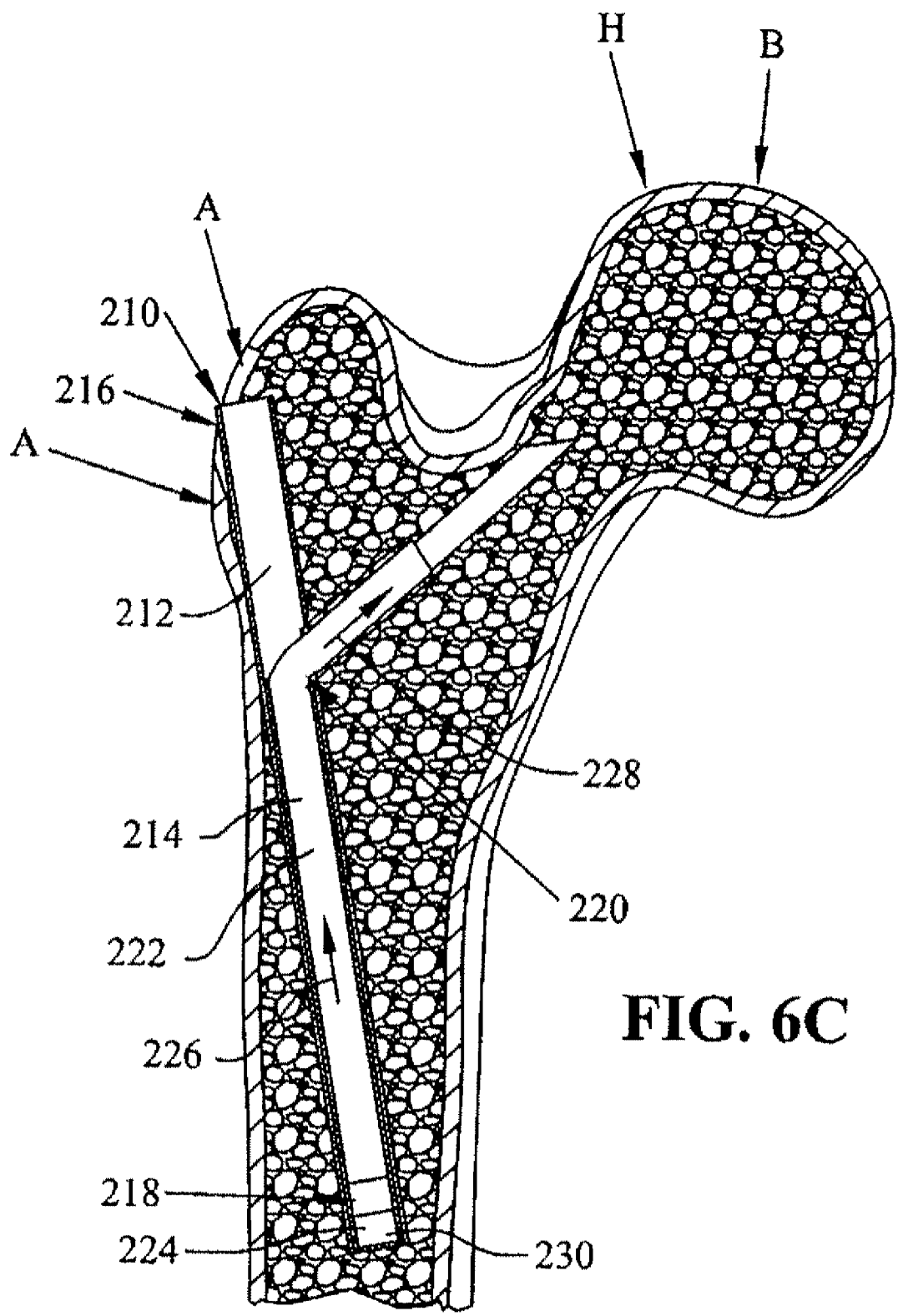

FIGS. 6A through 6C depict another embodiment of the apparatus, generally indicated by numeral 210. In the depicted embodiment, apparatus 210 includes a housing 212 and a support member assembly 214. Housing 212 has a substantially circular cross section and includes a proximal end 216, a distal end 218 and an opening 220. In the depicted embodiment, opening 220 is formed intermediate the proximal end 216 and the distal end 218.

In the depicted embodiment, support member assembly 214 includes a support member 222 and an actuator mechanism 224. Actuator mechanism 224 may be any suitable mechanism configured to propel support member 222 in the direction of arrow 226. For example, actuator mechanism 224 may include a motor 230 and a threaded member (not shown) connected to the support member 222. The motor 230 may rotate the threaded member, and the rotation of the threaded member may cause support member 222 to traverse the threaded member and move in the direction of arrow 226.

With reference still to FIGS. 6A through 6C, apparatus 210 may be inserted into an aperture A formed in bone B while support member 222 is fully positioned within housing 21 2 as illustrated in FIG. 6A. Once the apparatus 210 is located at a desired position within bone B, actuator mechanism 224 may be activated in a suitable manner to direct support member 222 in the direction of arrow 226. In addition, housing 212 may include a diffusion plate, such as diffusion plate 320 shown in FIG. 7, that is configured to direct support member 222 in the direction of arrow 228 and through opening 220. Accordingly, actuator mechanism 224 may drive support member 222 into the femoral head H through opening 220. It should be noted that in embodiments, support member 222 may be a telescoping member in which actuator mechanism 224 is capable of causing support member 222 to telescope and retract as necessary.

Figure 7:
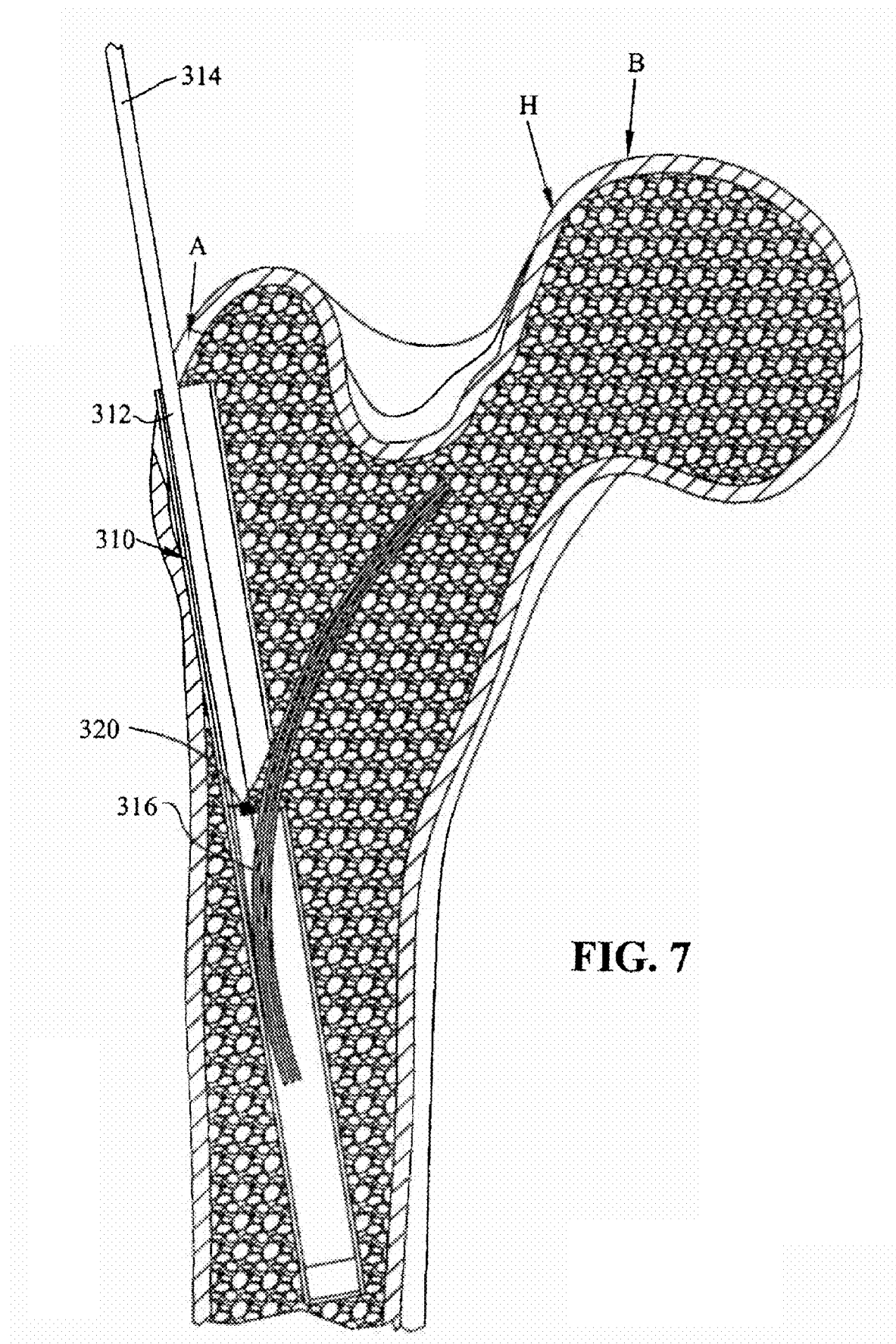
FIG. 7 is a sectional view of another embodiment of a support apparatus, shown inserted into a bone.

With reference now to FIG. 7, another embodiment of the support apparatus, indicated by numeral 310, is depicted. In the depicted embodiment, apparatus 310 includes a housing 312, a cable 314 and a support member 316. The configuration of apparatus 310 is similar to that described above with respect to other embodiments. Specifically, cable 314 extends through housing 312 and is connected to the distal end of member 316. In the depicted embodiment, support member 316 is a stack a leaf spring plates. Support member 316 may be formed in any suitable manner, and in a manner similar to that described above, the support member 3 16 may be moved into the femoral head and neck H by cable 314 in order to provide additional strength and support to the femoral head and neck H. The leaf spring plates may be formed from any suitable biocompatible material, such as nitinol, for example. Additionally, support apparatus 310 may include a diffusion plate 320 that is configured to direct support member 316 out of housing 312 and into femoral head and neck H.

Figure 8A:
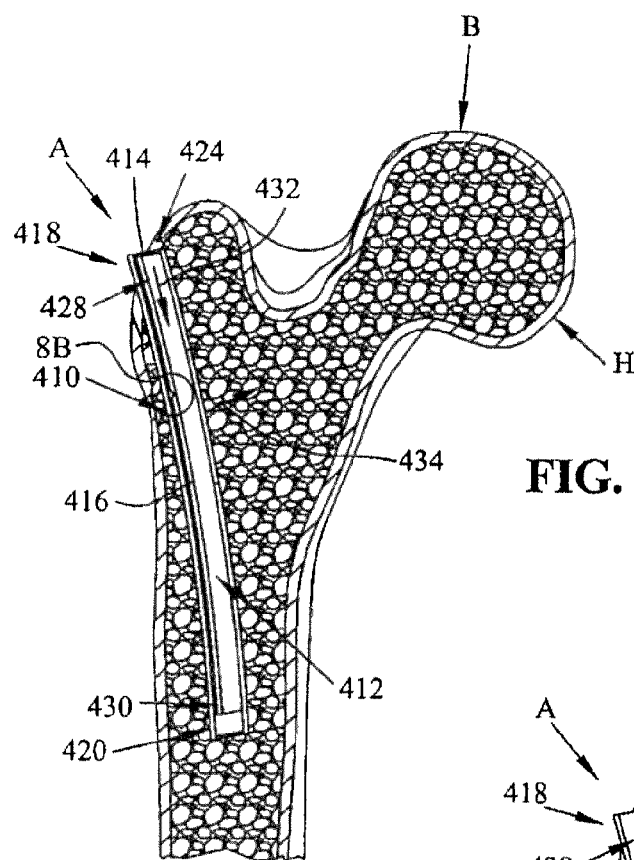
FIGS. 8A-8C are sequential views showing the insertion and deployment into a bone of the support apparatus of FIG. 7.
Figure 8B:
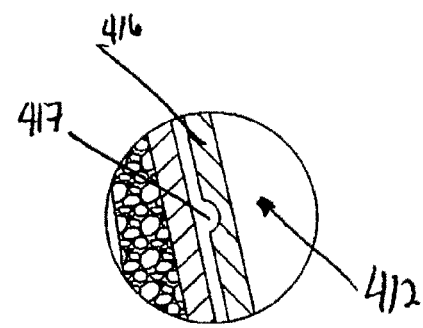
Figure 8C:
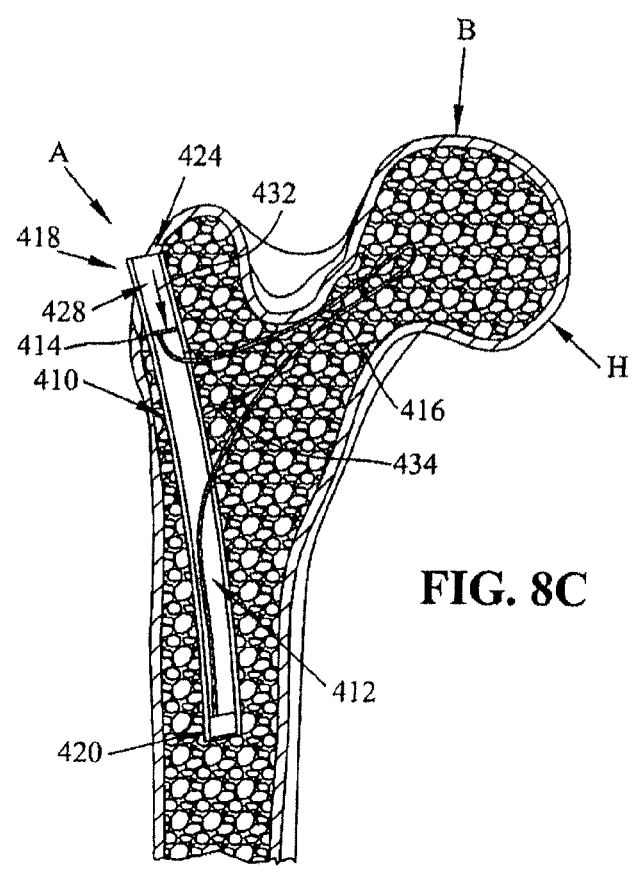

With reference now to FIGS. 8A through 8C, an embodiment of an apparatus is generally indicated by numeral 410. In the depicted embodiment, apparatus 410 includes a housing 412, a actuator 414 and support member 416. Housing 412 has a substantially circular cross section and includes a proximal end 418 and a distal end 420. Housing 412 further includes an opening 422 formed as a slot intermediate the proximal end 418 and the distal end 420 and an opening 424 formed at the proximal end 418.

In the depicted embodiment, actuator 414 is configured to traverse housing 412. Specifically, actuator 414 may move from proximal end 418 in the direction of opening 422. Actuator 414 may be driven in any suitable manner. For example, the interior surface of housing 412 may be threaded and actuation of the actuator 414 may cause actuator 414 to traverse the threads. In some embodiments, a cable (not shown) may be employed to cause actuator 414 to traverse housing 412.

Referring still to FIGS. 8A through 8C, support member 416 includes a proximal end 428 and a distal end 430. Support member 416 further includes a notch 417 located intermediate the proximal end 428 and the distal end 430. Distal end 430 is affixed to housing 412 in any manner ensuring that distal end 430 remains in a relatively fixed position with respect to housing 412. Proximal end 428 of support member 416 is connected to actuator 414 in any suitable manner. Proximal end 428 is configured to travel with actuator 414 as the actuator 414 moves within housing 412.

Support member 416 is configured to flex in a manner allowing a portion of the support member 416 to extend out of opening 422 as necessary. In the depicted embodiment, support member 416 flexes at notch 417. For example, when actuator 414 is moved in the direction of arrow 432, the proximal end 428 of support member 416 approaches the distal end 430. Since distal end 430 is fixed, the movement of proximal end 428 results in a portion of support member 416 moving in the direction of arrow 434 and extending out from opening 422.

In operation, a surgeon may insert apparatus 410 into bone B through aperture A. Similar to the examples described above, bone B is a femur and includes a femoral head and neck H, and apparatus 410 is inserted into an aperture A near the greater trochanter of the proximal femur formed by a drill, for example. Once the apparatus 410 has been located in the desired position within bone B, the surgeon may move actuator 414 in the direction of arrow 432. As actuator 414 moves in the direction of arrow 432, the proximal end 428 moves in the direction of arrow 432 also, and a portion of the support member 416 extends outward from opening 422 in the direction of arrow 434 and into the femoral head and neck H. The support member 416 strengthens the femoral head and neck H and provides additional support.

It should be noted that proximal end 428 of support member 416 may be fixed within the housing 412 and distal end 430 may be connected to an actuator. In these embodiments, once the apparatus 410 has been inserted into bone B, the surgeon may move the actuator in the direction opposite arrow 432, thereby causing movement of distal end 430. Since proximal end 428 remains fixed within housing 412, the movement of distal end 430 in the direction opposite arrow 432 will cause a portion of support member 416 to extend outward from opening 422 in the direction of arrow 434. Furthermore, it should be noted that in embodiments of the invention, support member 416 may be configured so that both ends of the support member 416 move with respect to the housing 412. In a manner similar to that described above, the support member 416 will support and strengthen the femoral head H.

Figure 9A:
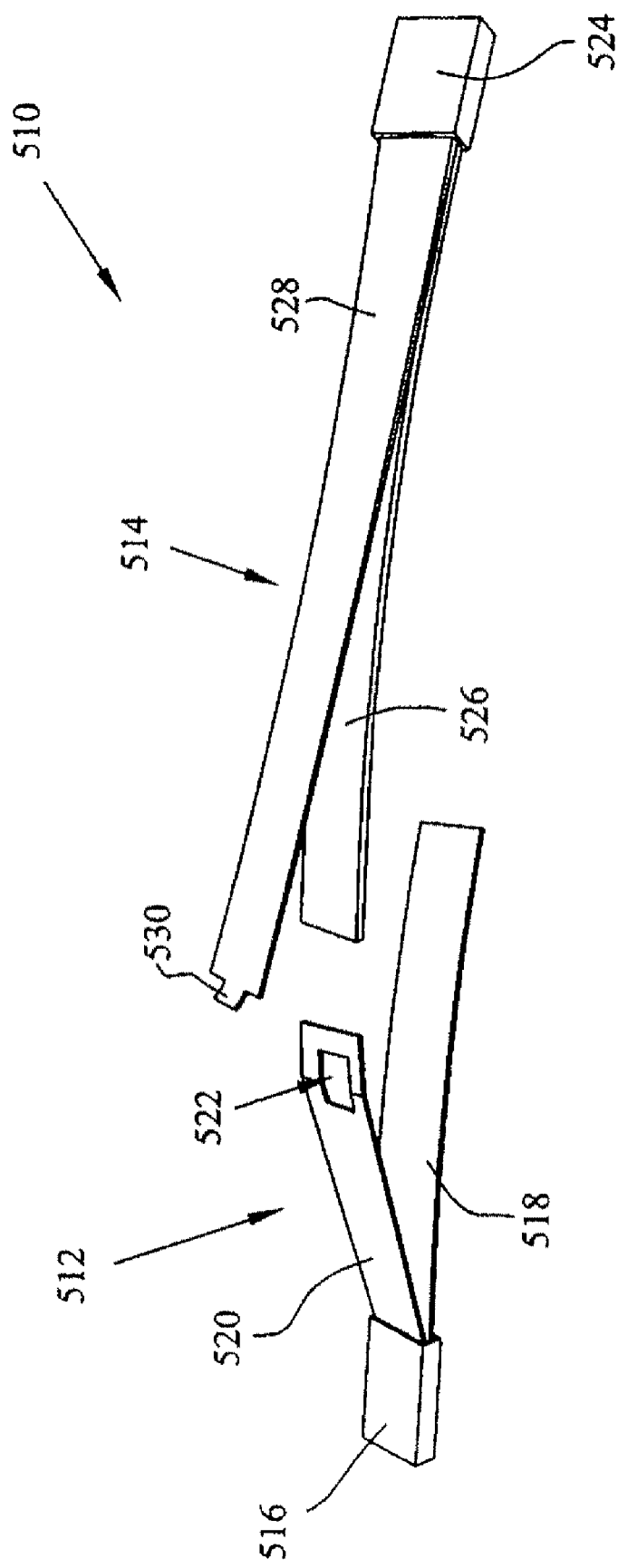
FIG. 9A is a perspective view of another embodiment of a support apparatus.
Figure 9B:
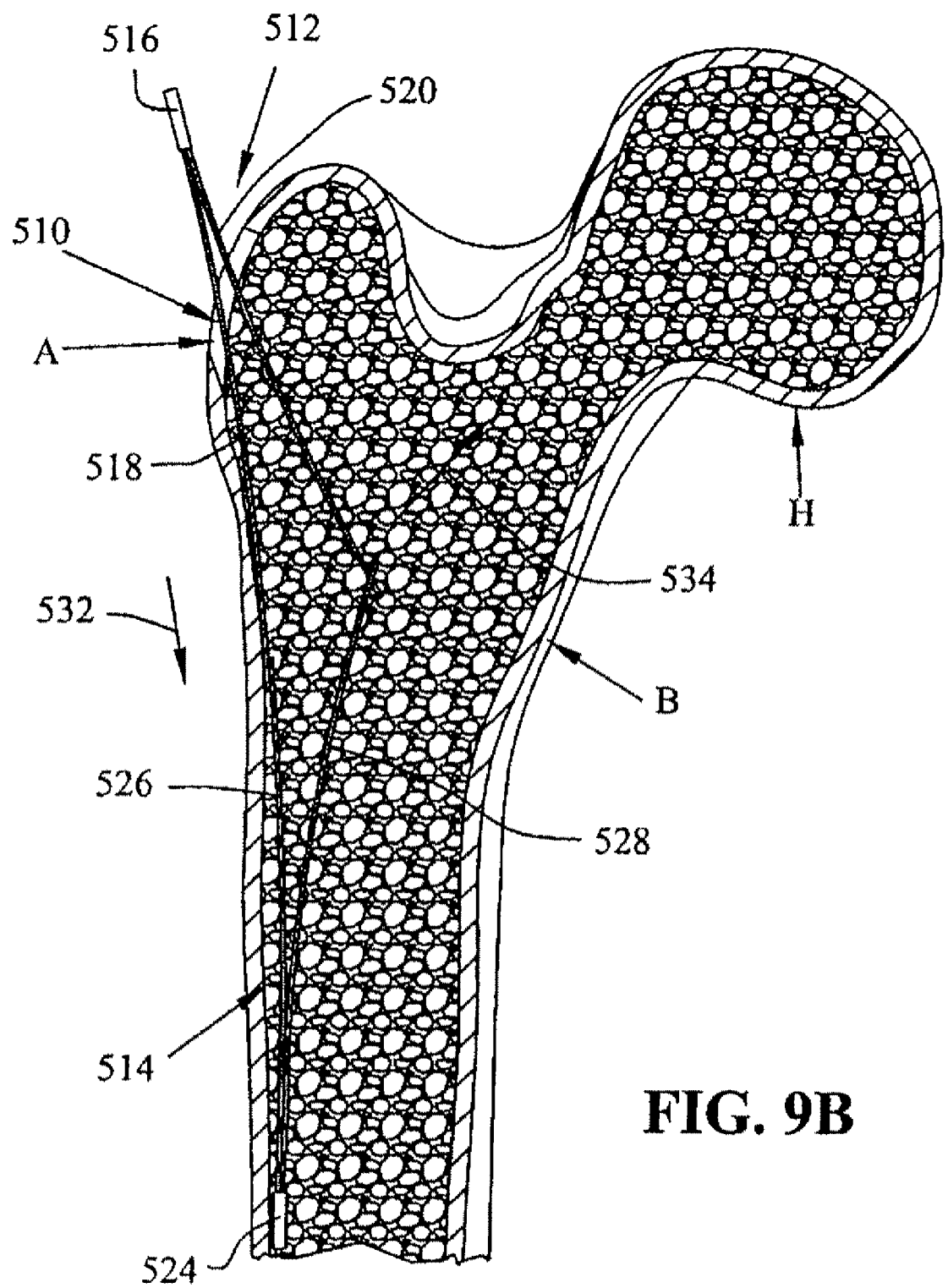
FIGS. 9B and 9C are sequential views showing the insertion and deployment into a bone of the support apparatus of FIG. 9A.
Figure 9C:
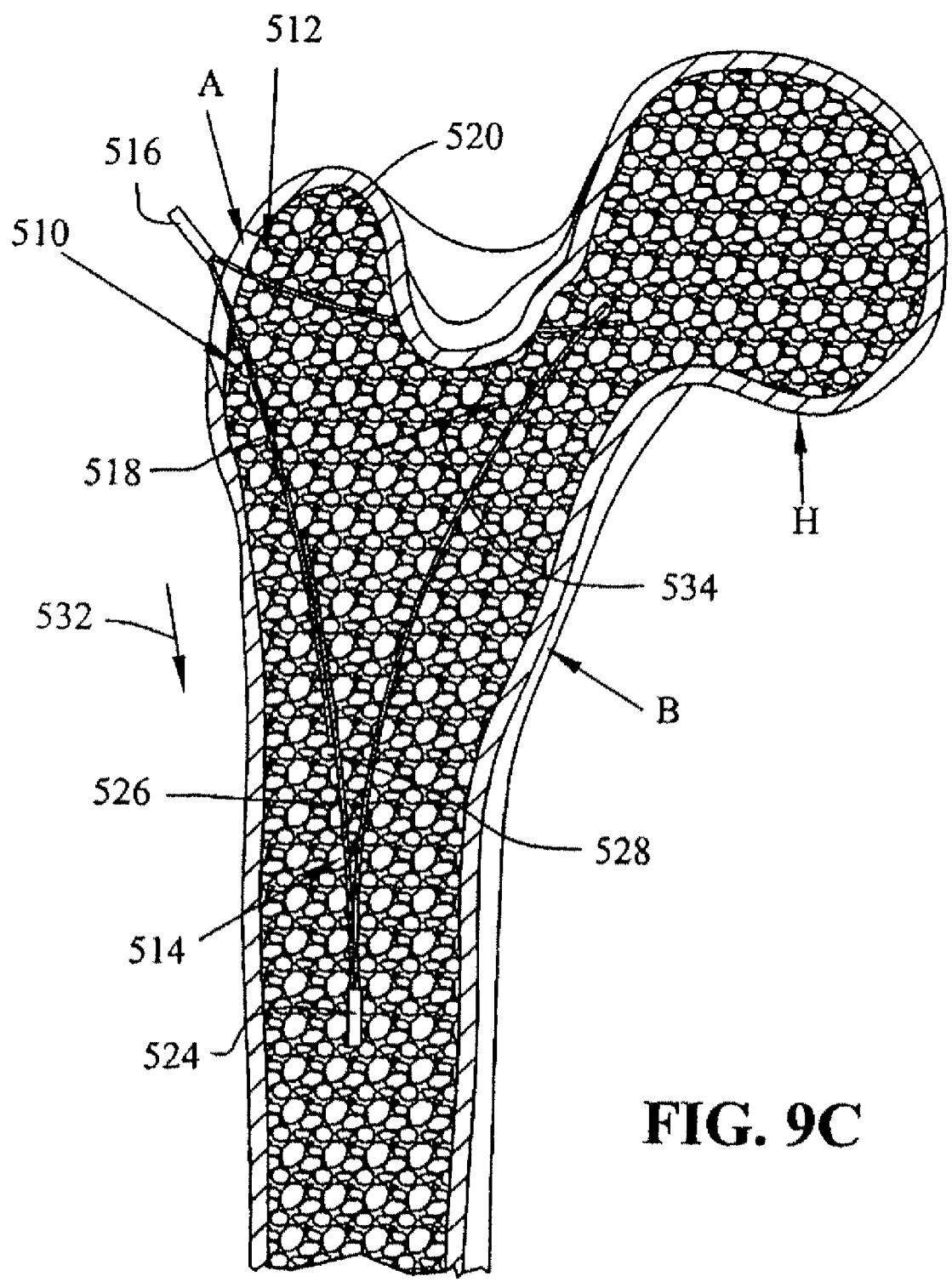

With reference now to FIGS. 9A through 9C, another embodiment of an apparatus is indicated by numeral 510. In the depicted embodiment, apparatus 510 includes a first support member assembly 512 and a second support member assembly 514. First support member assembly 512 includes a hub 516 from which extends a first extension 518 and a second extension 520. Hub 516 may be formed from any suitable material capable of retaining the ends of the extensions 518, 520 together. In the depicted embodiment, first extension 518 is substantially flat, and second extension 520 is substantially flat. Second extension 520 includes an aperture 522.

Second support member 514 includes a hub 524, a first extension 526 and a second extension 528. First extension 526 and second extension 528 both extend outward from hub 524. First extension 526 and second extension 528 are both substantially flat. Second extension 528 includes a raised member 530, and raised member 530 is sized and configured to be received by aperture 522.

In order to assemble apparatus 510, a surgeon inserts member 530 into aperture 522. The hubs 516, 524 are then moved apart from each other, which results in the first extensions 518, 526 of the support member assemblies 512, 514 moving closer to the second extensions 520, 528 to form a collapsed structure.

In operation, as shown in FIG. 9B, a surgeon may insert apparatus 510 in its collapsed state into a bone B through an aperture A in the direction of arrow 532. In the depicted embodiment, bone B is a femur and a drill forms aperture A in the greater trochanter of the proximal femur in any suitable manner.

In some embodiments, second support member assembly 514 may be inserted into bone B first. Once second support member assembly 514 has reached a desired location, hub 524 may be affixed within the intramedullary canal in a suitable manner, such as with one or more bone screws, for example. After hub 524 has been set in a fixed position with respect to the bone B, the health care professional may continue to move hub 516 in the direction of arrow 532 to deploy the device. The movement of hub 516 in the direction of arrow 532 will cause the second extensions 520, 528 to move in the direction of arrow 534, thereby allowing the extensions 520, 528 to project outwardly into, and substantially fill the area of the femoral head and neck H. The presence of the extensions 520, 528 strengthen and support femoral the head and neck H.

Figure 10:
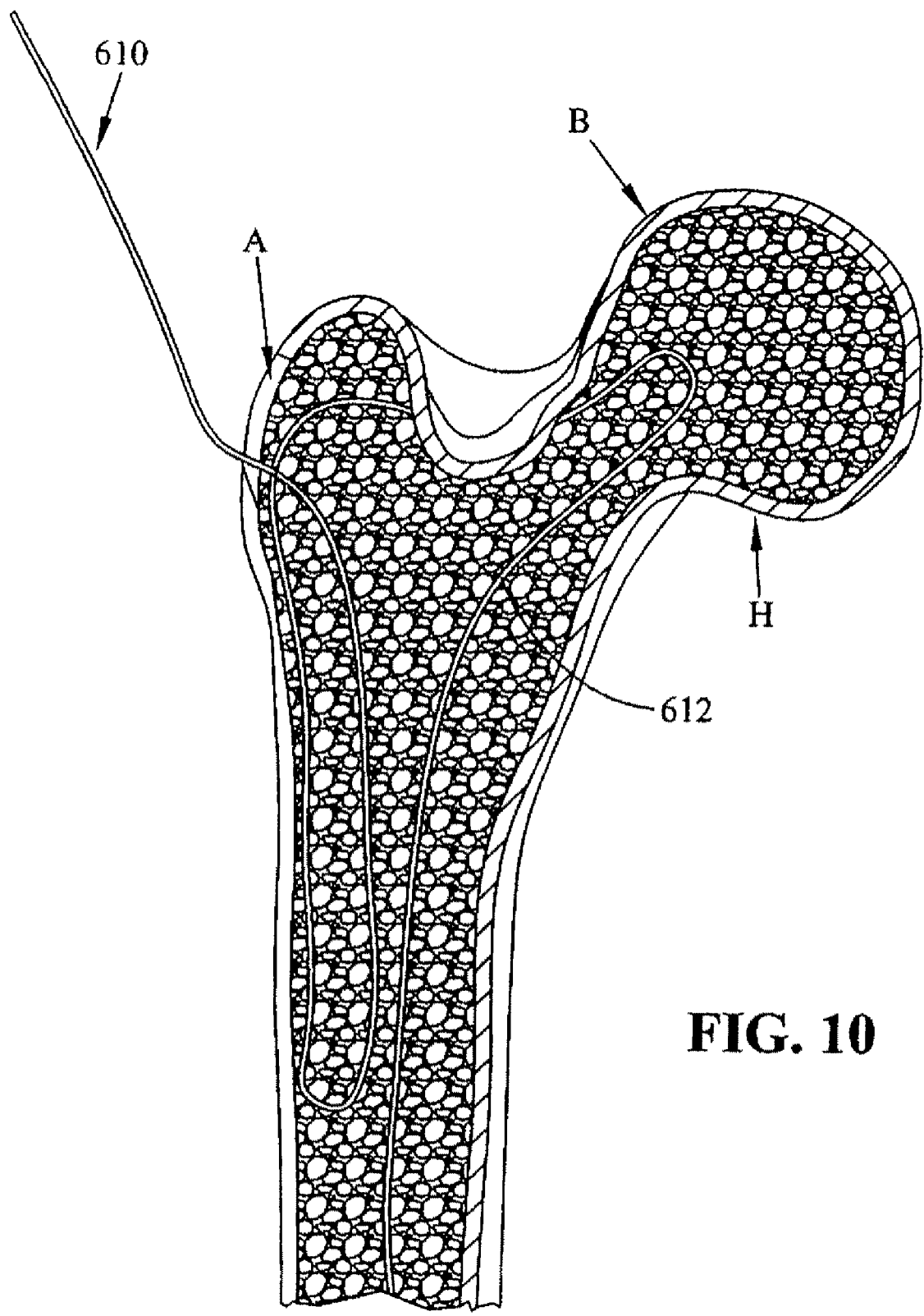
FIG. 10 is a sectional view of a bone including another embodiment of a support apparatus.

FIG. 10 depicts an apparatus 610 comprising a nickel titanium, or nitinol, wire. Nitinol is a shape memory alloy that is super elastic above a pre-determined temperature and readily capable of deformation. Below the pre-determined temperature, the nitinol retains it shape and does not readily deform. In the present embodiment, apparatus 610 may be inserted into bone B through aperture A. As long as the temperature of apparatus 610 remains above the pre-determined temperature, the apparatus 610 may be formed in any desired shape, with a portion 612 of apparatus 610 being located in the femoral head and neck H. The portion 612 succeeds in providing support to and strengthening the femoral head and neck H.

Figure 11:
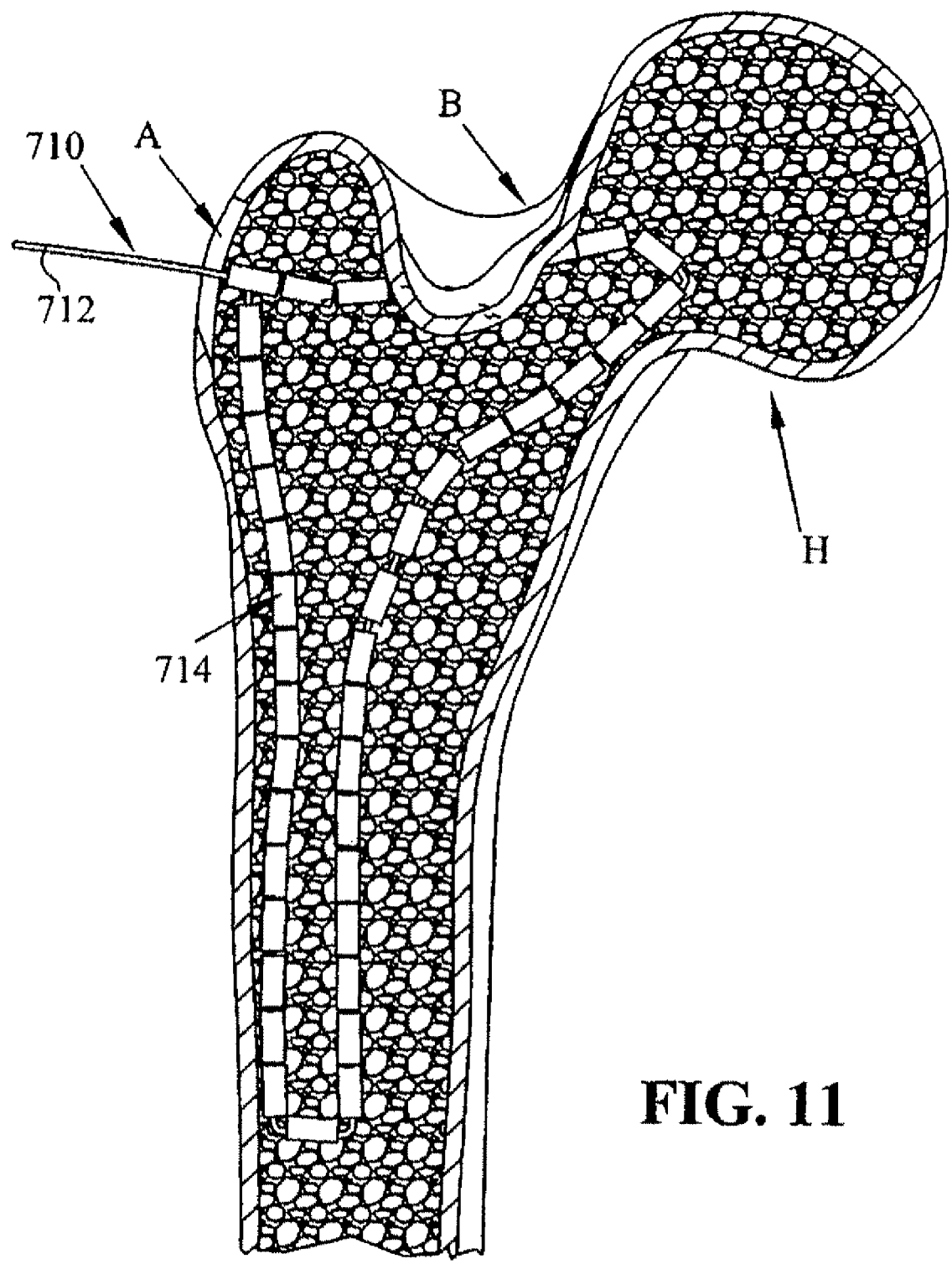
FIG. 11 is a sectional view of a bone including another embodiment of a support apparatus.

FIG. 11 depicts an apparatus 710 comprising a nickel titanium, or nitinol, wire, indicated by numeral 712 encompassed by a plurality of plastic members, generally indicated by numeral 714. The depicted embodiment of the invention functions in a manner substantially identical to that described above with respect to apparatus 610. In the depicted embodiment, the plastic members 714 provide support to the wire 712 after the wire has been positioned in the femoral head and neck H.

Referring still to FIG. 11, when the wire 712 is not under tension, the apparatus 710 remains flexible since the members 714 are capable of rotating with respect to each other. Once the wire 712 is under tension, the members 714 are forced against each other and the apparatus 710 becomes rigid. In one embodiment, the faces of each of the members 714 include interlocking features allowing the members 714 to become interlocked with adjacent members 714 when the wire 712 is under tension. The interlocking of the members 714 causes the apparatus 710 to remain substantially rigid. The members 714 may include cutting features (not shown) that would aid in insertion by cutting the cancellous bone.

Apparatus 710 may be inserted into bone B through aperture A formed in the greater trochanter of the depicted femur. The apparatus 710 may travel through the bone B proximate the lateral wall. Once the apparatus 710 has been fully inserted, the ends of the apparatus 710 may be moved to create tension on the wire 712, thereby forcing a portion of the apparatus 710 into the superior cortex through the femoral neck in order to provide strength to the bone B. In order to remove the apparatus 710, the tension may be released and the apparatus 710 may be withdrawn through the aperture A.

Figure 12:
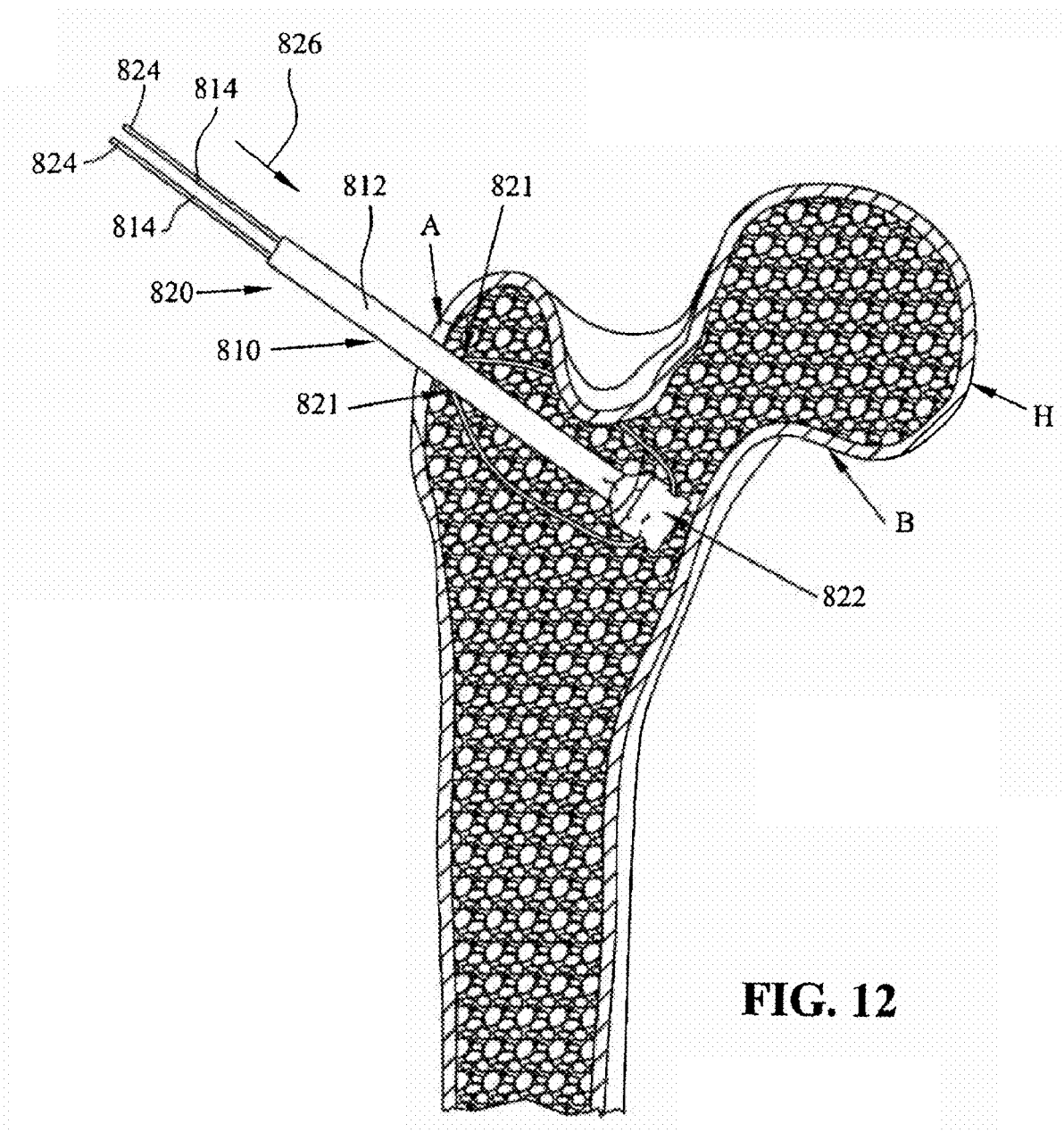
FIG. 12 is a sectional view of a bone including another embodiment of a support apparatus.
Figure 13:
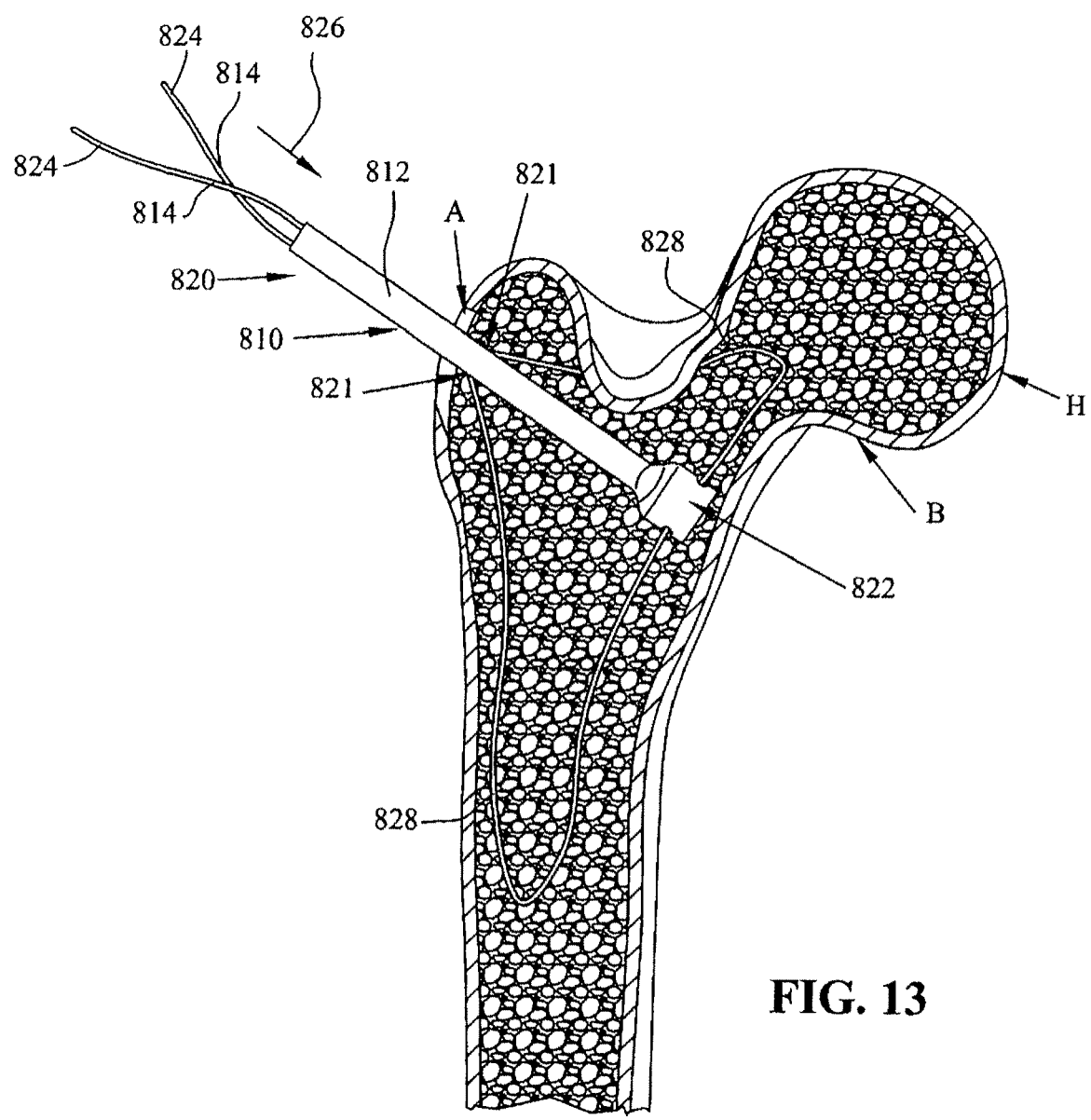
FIG. 13 is a sectional view of a bone showing the support apparatus of FIG. 12 in an extended, deployed position.

FIGS. 12 and 13 depict another embodiment of an apparatus indicated by numeral 810. Apparatus 810 includes a base member 812 and a pair of wires each indicated by numeral 814. The wires 814 are disposed entirely within the base member 812 from a proximal end 820 of the base member 812, and extend through a pair of holes 821 at the midpoint between the proximal end 820 and the distal end 822, and extend externally of base member 812. An end of the wires 814 are affixed to the distal end of the base member 812. In the depicted embodiment, the wires 814 may be manufactured from any suitable material, such as nitinol, for example.

In usage, a surgeon may insert apparatus 810 into an aperture A formed within a bone B. Once the apparatus 810 has been located in a desired position, the surgeon may then move the ends 824 of the wires 814 in the direction of arrow 826. As shown in FIG. 13, a portion 828 of the wires 814 will move into the femoral head and neck H in order to provide support and strengthen the area of the femoral head and neck H. Another portion of the wires 814 may move into the intramedullary canal in order to provide strength to the bone B. It should be noted that in some embodiments of the invention, the wires 814 may include a kink or a slot in order to ensure the wires 814 extend into the femoral head and neck H and the intramedullary canal. In addition, additional wires (not shown) may be added to the apparatus 810 in order to form a whisk shaped structure when the wires are deployed.

Figure 14:
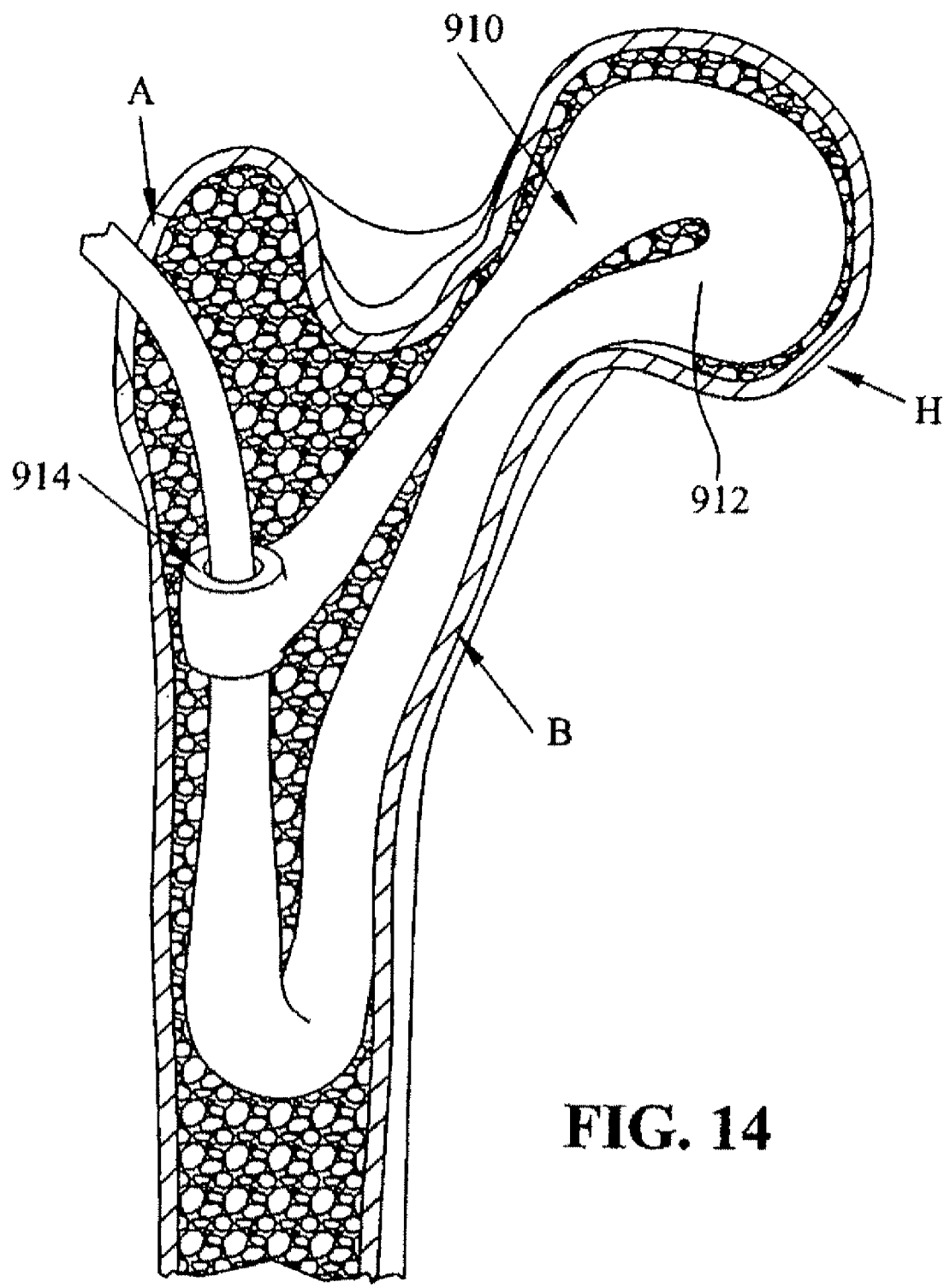
FIG. 14 is a sectional view of a bone including another embodiment of a support apparatus.

FIG. 14 depicts an apparatus generally indicated by numeral 910. Apparatus 910 includes a substantially tubular support member 912 including an aperture 914. As depicted in FIG. 14, apparatus 910 is configured to be inserted into bone B through aperture A. Once the support member 912 has been positioned within the bone B, the surgeon may fill the support member 912 with fluid thereby allowing the support member 912 to fill the femoral head and neck H area of the bone B.

It should be noted that in some embodiments, the apparatus 910 may be utilized in conjunction with various other embodiments described herein. For example, apparatus 910 may be attached to the wires 814 of apparatus 810 in an unfilled state. Once the wires 814 have been deployed and apparatus 910 has been forced into the femoral head and neck H and intramedullary canal along with the wires 814, the support member 912 may be filled with a fluid or a gel in order to provide structure to the proximal femur. In embodiments, the support member 912 may include baffles or a structure configured to provide strength to the femur.

Figure 15:
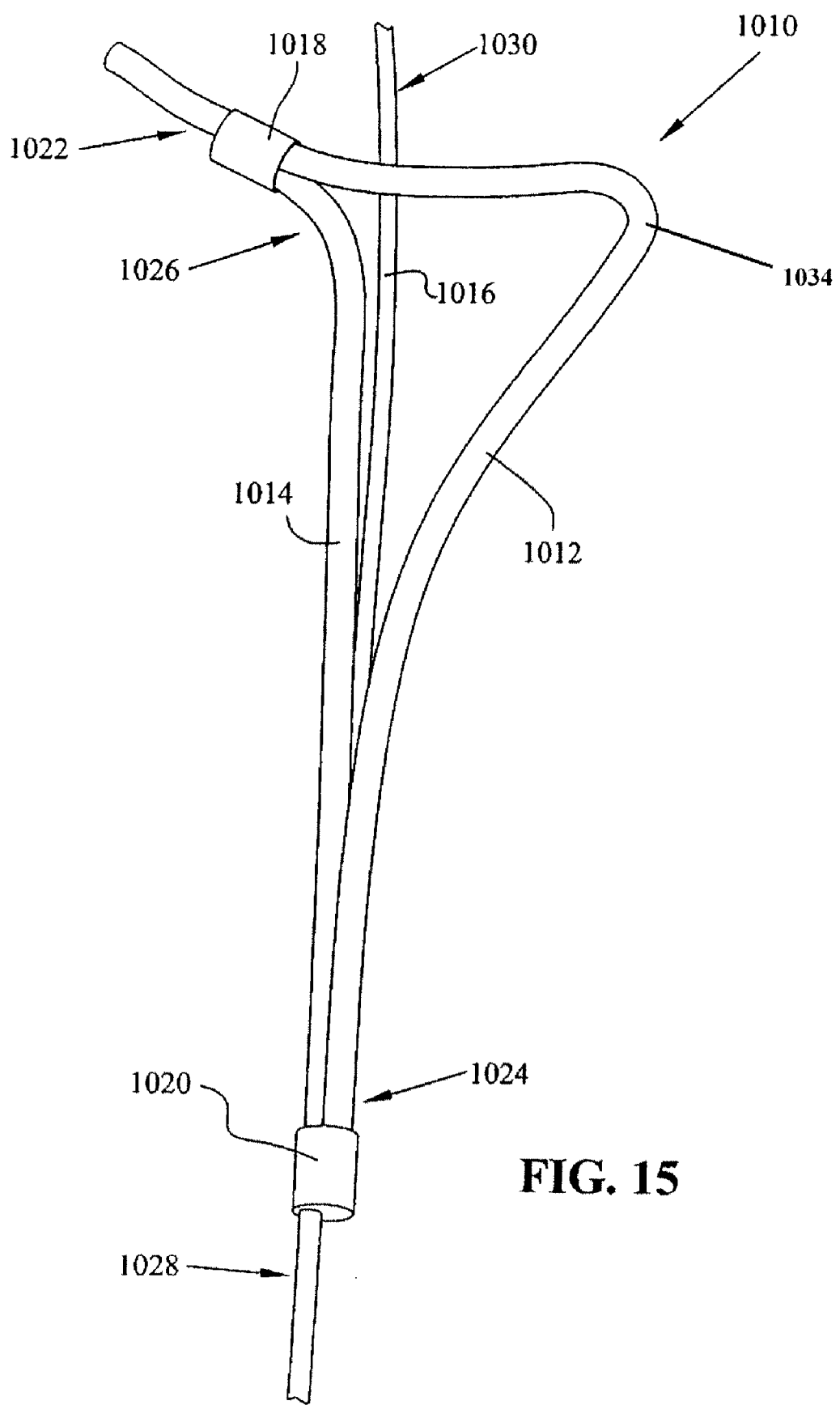
FIG. 15 is a front view of another embodiment of a support apparatus.

FIG. 15 depicts an embodiment of the apparatus indicated by numeral 1010. Apparatus 1010 includes a first wire 1012, a second wire 1014, a third wire 1016, a first member 1018 and a second member 1020. The wires 1012, 1014, 1016 may be manufactured from any suitable material, such as nitinol. The members 1018, 1020 may be manufactured from any suitable material, such as stainless steel.

Wire 1012 includes a proximal end 1022 and a distal end 1024. Distal end 1024 is received and retained by member 1020. Wire 1012 passes through member 1018. Member 1018 is configured so that member 1018 may traverse wire 1012.

Wire 1014 includes a proximal end 1026 and a distal end 1028. Proximal end 1026 is received and retained by member 1018, and wire 1014 passes through member 1020. Member 1020 is configured so that member 1020 may traverse wire 1014.

Wire 1016 includes a proximal end 1030 and a distal end (not shown). The distal end is received and retained by member 1020. In usage, proximal end 1026 of wire 1014 and the distal end of wire 1012 may be moved apart, thereby causing the three wires 10 12, 1014, 1016 to extend substantially parallel. With the wires 1012, 1014, 1016 arranged parallel, the apparatus 1010 may be inserted into a bone through an aperture in a manner similar to that described above with respect to previous embodiments. Once the apparatus has been inserted into the bone, the proximal end 1022 of wire 1012 may be moved in the direction of member 1020 thereby causing a portion 1034 of the wire 1012 to extend into the femoral head in order to provide support and strengthen the femoral head. In embodiments of the invention, the wires 1012, 1014, 1016 may include a notch configured to make the wires 1012, 1014, 1016 extend in a desired direction.

Figure 16:
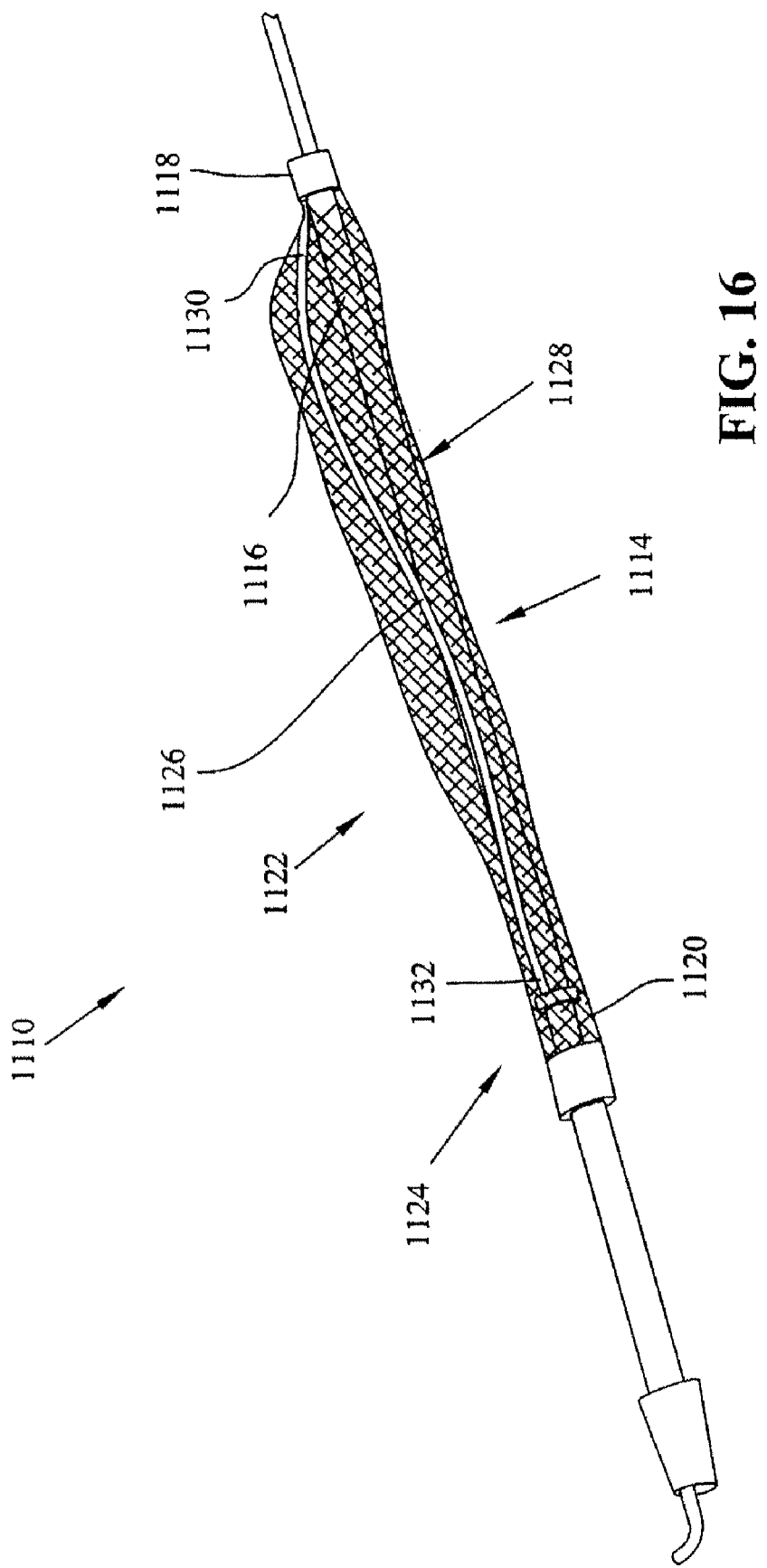
FIGS. 16 and 17 are perspective views of another embodiment of a support apparatus in undeployed and deployed configurations, respectively.
Figure 17:
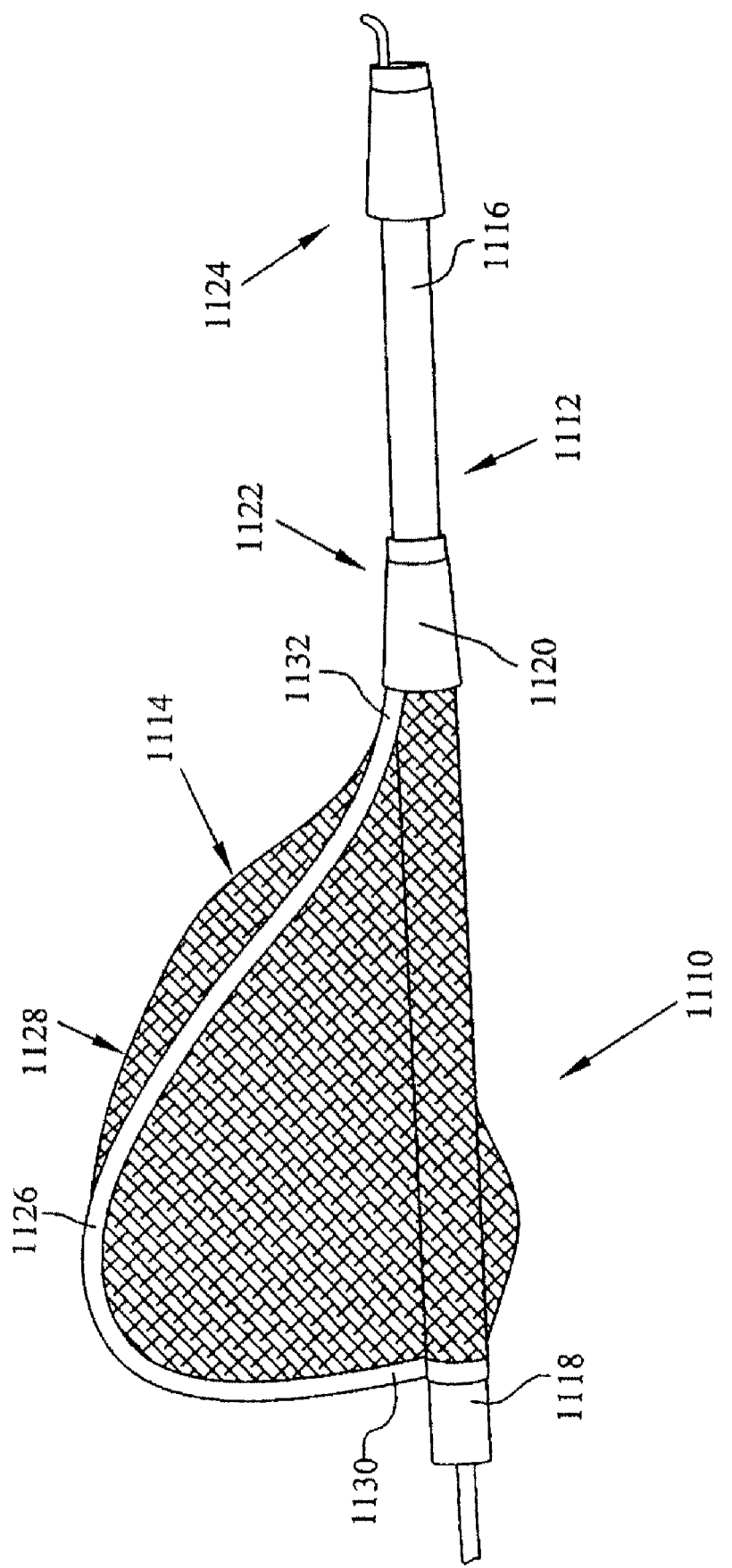

FIGS. 16 and 17 depict another embodiment of an apparatus, generally indicated by numeral 1110. Apparatus 1110 includes an elongated assembly 1112 and a wire assembly 1114. In the depicted embodiment, the elongated assembly 1112 includes a rod member 1116, a fixed member 1118 and a moveable member 1120. The fixed member 1118 is fixed in position with respect to the rod member 1116. The moveable member 1120 is capable of traversing rod member 1116 between a first position, indicated by numeral 1122, and a second position, indicated by numeral 1124.

In the depicted embodiment, the wire assembly 1114 includes a wire 1126 and a mesh portion 1128. Wire 1126 includes a proximal end 1130 and a distal end 1132. Proximal end 1130 is connected to the fixed member 1118, and distal end 1132 is connected to the moveable member 1120. Mesh portion 1128 is connected to the wire 1126 and the rod member 1116 in a suitable manner.

As shown in FIG. 16, when the moveable member 1120 is in the first position 1124, the wire 1126 is located proximate the rod member 1116. When the moveable member 1120 is in the second position 1122, the wire is forced away from the rod member 1116, as shown in FIG. 17. Accordingly, the moveable member 1120 may be moved into the first position 1124 in order to allow the apparatus 1110 to be inserted into an aperture of a bone. Once the apparatus has been positioned within the bone, the moveable member 1120 may be moved into the second position 1122 thereby forcing a portion of the wire 1126 and the mesh 1128 into a portion of the bone. The presence of the wire 1126 and the mesh 1128 may provide additional strength and support to the bone.

Figure 18:
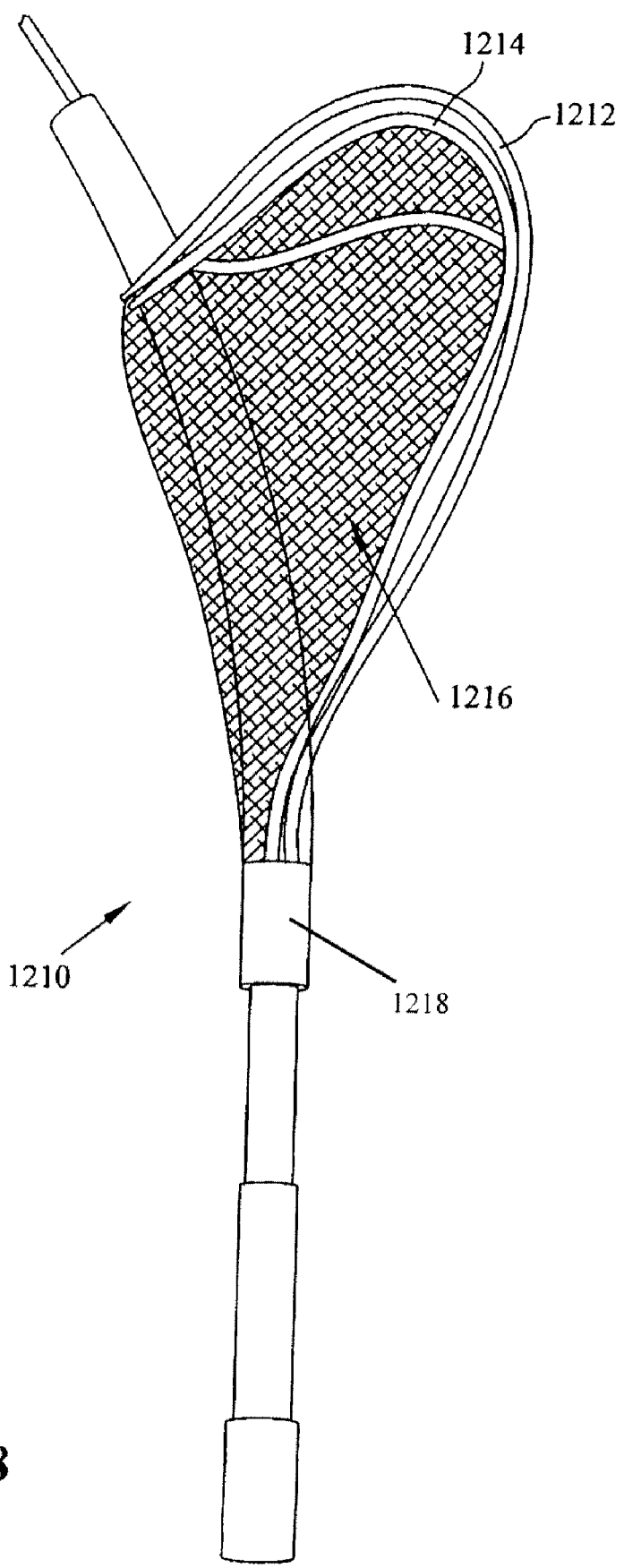
FIG. 18 is a perspective view of another embodiment of a support apparatus shown in a deployed position.

As shown in FIG. 18, another embodiment of an apparatus indicated by numeral 1210 is depicted. Apparatus 1210 is similar to apparatus 1110, described above. Apparatus 1210 includes two wires 1212, 1214 interconnected with a mesh portion 1216. In a manner similar to that described above, the position of the wires 1212, 1214 are controlled by the moveable member 1218.

Figure 19:
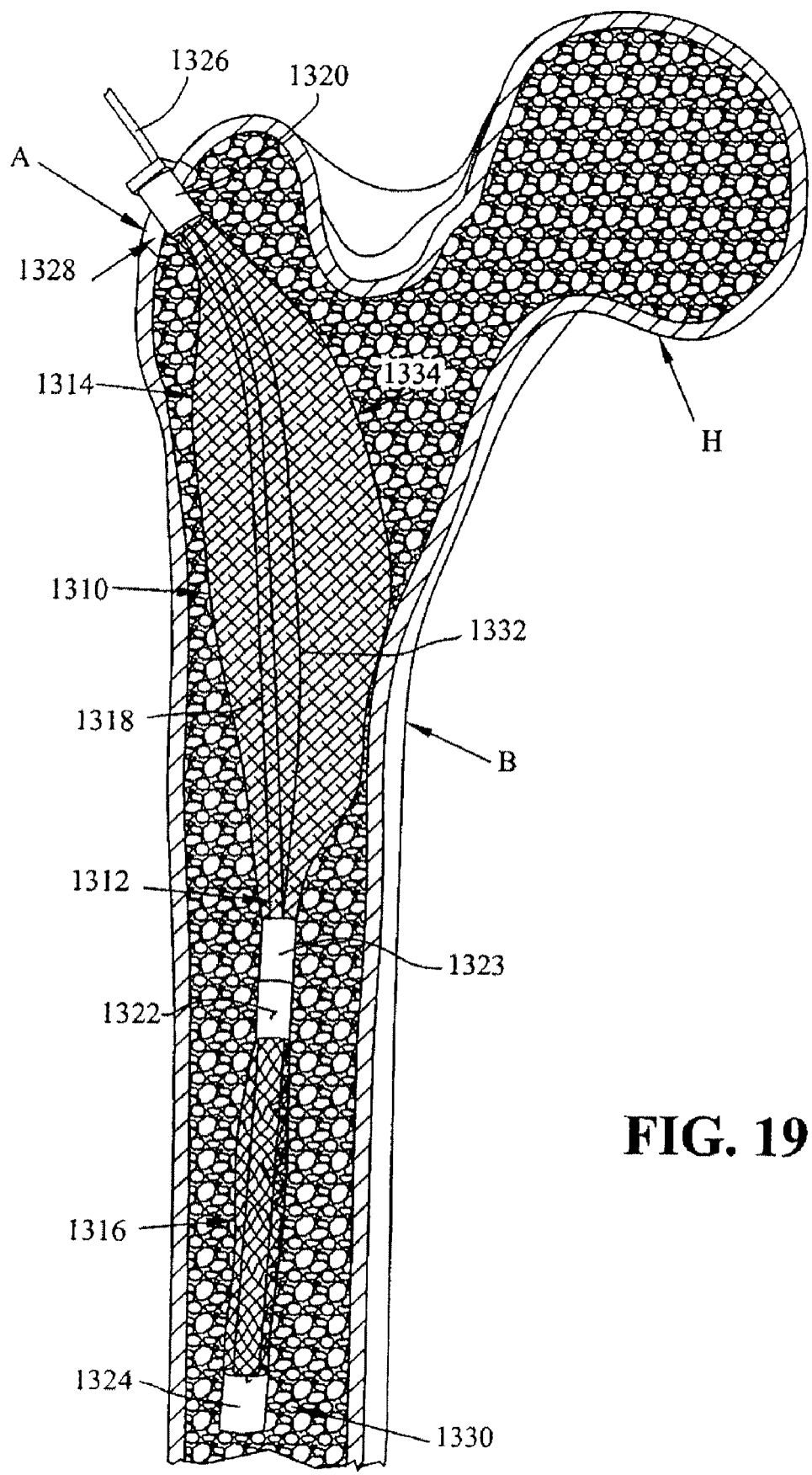
FIGS. 19 and 20 are sectional views of a bone including another embodiment of a support apparatus.
Figure 20:
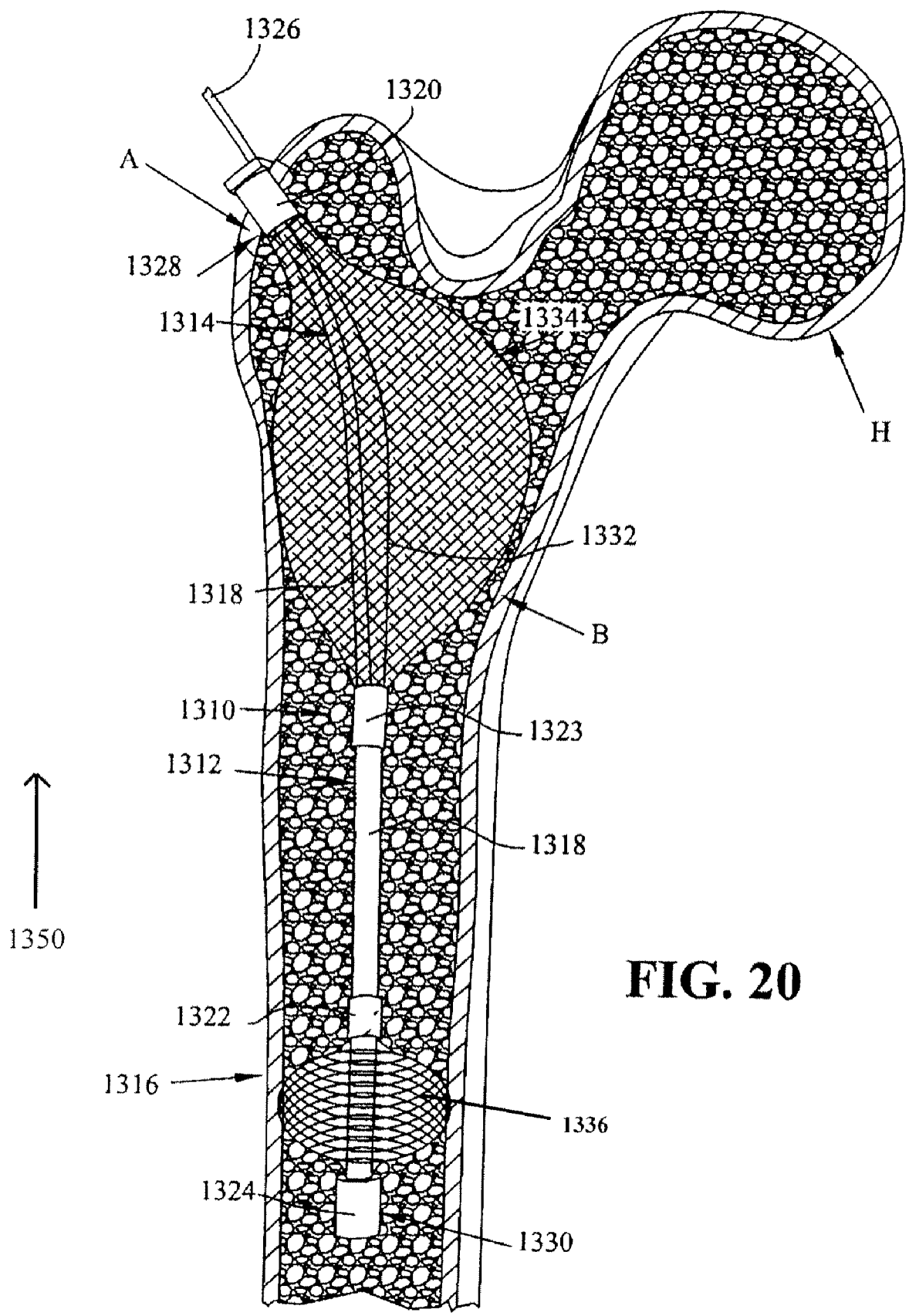

FIGS. 19 and 20 depict another embodiment of an apparatus indicated by numeral 1310. Apparatus 1310 includes a rod assembly 1312, a wire assembly 1314 and anchoring assembly 1316. In the depicted embodiment, rod assembly 1312 includes a rod member 1318, a first fixed member 1320, a second fixed member 1322, a first moveable member 1323, a second moveable member 1324, and a cable 1326.

Rod member 1318 is substantially hollow and includes a proximal end 1328 and a distal end 1330. The fixed members 1320, 1322 are affixed to rod member 1318 in a manner preventing the members 1320,1322 from traversing rod member 1318. Cable 1326 extends through the rod member 1318 and connects to the moveable members 1323, 1324 in a suitable manner. The moveable members 1323, 1324 move as the cable 1326 moves. Accordingly, the moveable members 1323, 1324 move with respect to the fixed members 1320, 1322 as the cable 1326 is moved.

In the depicted embodiment, wire assembly 1314 includes a wire 1332 and a mesh portion 1334. Mesh portion 1334 may be attached to the wire 1332 in any conventional manner. Wire 1332 is connected to the fixed members 1320, 1322 and moveable member 1323. The wire 1332 is configured to move as the moveable member 1327 moves.

Referring still to FIGS. 19 and 20, mesh portion 1334 is connected to fixed member 1320 and moveable member 1323. The mesh portion 1334 is configured to move as the moveable member 1323 moves.

Referring still to FIGS. 19 and 20, anchoring assembly 1316 includes a mesh portion 1336. In the depicted embodiment, mesh portion 1336 extends between the members 1322, 1324. As illustrated by FIGS. 19 and 20, as the moveable member 1324 moves in the direction of member 1322, the mesh portion 1336 extends outward away from rod member 1318. The mesh portion 1336 may be manufactured from a material allowing the mesh portion 1336 to engage the interior surface of a bone.

In operation, the cable 1316 is connected to and controls the position of the moveable members 1323, 1324 with respect to the fixed members 1320, 1322. When the cable 1316 is moved in the direction of arrow 1350, the moveable members 1323, 1324 also traverse rod member 1318 in the direction of arrow 1350. The movement of the moveable members 1323, 1324 in the direction of arrow 1350 causes the ends of the mesh portions 1334, 1336 to come together. As illustrated in FIG. 20, as the ends of the mesh portions 1334, 1336 come together, the mesh portions 1334, 1336 will flare outward. In addition, when cable 1316 is moved in the direction opposite arrow 1350, the moveable members 1323, 1324 move in the opposite direction and the mesh portions 1334, 1336 move adjacent to rod member 1318.

Accordingly, cable 1316 may be used to position the mesh portions 1334, 1336 adjacent to the rod member 1318. With the mesh portions 1334, 1336 located adjacent the rod member 1318, the apparatus 13 10 may then be inserted into the intramedullary canal of bone B through an aperture A. In the depicted example, bone B is a femur including a femoral head and neck H.

Once the apparatus 1310 has been properly positioned within the bone B, the cable 1316 may be moved in the direction of arrow 1350. As explained above, this movement results in the mesh portions 1334, 1336 flaring outward, as depicted in FIG. 20. Mesh portion 1334 enters the femoral head and neck H in order to provide support to the bone B. In addition, mesh portion 1336 may engage the interior of the bone B and provide a receiving area for the bone screw or similar device capable of affixing apparatus 13 10 to the bone B.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of strengthening and supporting a proximal femur of a patient, the patient's proximal femur including a shaft that defines an intramedullary canal and a head that extends medially from the shaft, the method comprising the steps of:
    providing an apparatus including a housing, a support member, and an actuator operably coupled to the support member, wherein the housing includes a proximal end and a distal end;
    implanting the housing into the intramedullary canal of the patient's proximal femur, and
    operating the actuator to move the support member between a first, undeployed position in which the support member is disposed proximate the housing and a second, deployed position in which the support member extends from the housing and into the head of the patient's proximal femur, wherein the operating step comprises pulling the actuator proximally toward the proximal end of the housing to move the support member from the first position. To the second position.

2. The method of claim 1, wherein the housing includes a proximal end and a distal end, the housing defining an opening at a location between the proximal end and the distal end, wherein the support member is located within the housing in the first position and the support member at least partially extends through the opening of the housing in the second position.

3. The method of claim 2, wherein the proximal end of the housing defines a second opening, and wherein the operating step comprises moving the actuator through the second opening of the housing.

4. The method of claim 1, wherein the implanting step occurs prophylactically before the patient's proximal femur fractures.

5. The method of claim 1, further comprising the step of identifying the patient as being at high risk of experiencing a fracture of the proximal femur before the implanting step.

6. A method of strengthening and supporting a proximal femur of a patient, the patient's proximal femur including a shaft that defines an intramedullary canal and a head that extends medially from the shaft, the method comprising the steps of:
    providing an apparatus including a housing, a support member, and an actuator operably coupled to the support member, the housing having a proximal end and a distal end, the housing defining an opening at a location between the proximal end and the distal end;
    implanting the distal end of the housing into the intramedullary canal of the patient's proximal femur with the support member in a first configuration, the support member being located substantially within the housing in the first configuration; and
    operating the actuator to adjust the support member from the first configuration to a second configuration, the support member extending through the opening in the housing and into the head of the patient's proximal femur in the second configuration, wherein the operating step comprises at least one of pulling the actuator proximally and pushing the actuator distally.

7. The method of claim 6, wherein at least a portion of the actuator is positioned external to the intramedullary canal of the patient's proximal femur such that the operating step is performed at a location external to the intramedullary canal of the patient's proximal femur.

8. The method of claim 6, wherein in the first configuration, the support member is located proximate to the distal end of the housing.

9. The method of claim 6, wherein the support member translates proximally through the housing during the operating step.

10. The method of claim 6, wherein the apparatus further includes an inclined surface located within the housing, wherein the support member interacts with the inclined surface to divert the support member at an angle as the support member moves from the first configuration to the second configuration.

11. The method of claim 6 further comprising the step of forming an aperture in the patient's proximal femur, wherein the implanting step comprises inserting the housing through the aperture and into the intramedullary canal of the patient's proximal femur.

12. The method of claim 11, wherein the forming step comprises forming the aperture in a greater trochanter of the patient's proximal femur.

13. The method of claim 6, wherein the implanting step comprises locating the opening of the housing entirely within the intramedullary canal of the patient's proximal femur.

14. The method of claim 6, wherein the implanting step occurs prophylactically before the patient's proximal femur fractures.

15. A method of strengthening and supporting a proximal femur of a patient, the patient's proximal femur including a shaft that defines an intramedullary canal, a greater trochanter that extends proximally from the shaft and a head that extends medially from the shaft, the method comprising the steps of:

providing an apparatus including a housing, a support member, and an actuator operably coupled to the support member, the housing having a proximal end and a distal end, the housing defining an opening at a location between the proximal end and the distal end;

identifying the patient as being at high risk of experiencing a fracture of the proximal femur:

forming an aperture in the patient's proximal femur, wherein the aperture is the only aperture formed in the patient's proximal femur;

implanting the distal end of the housing through the aperture and into the intramedullary canal of the patient's proximal femur with the support member in a first configuration, the support member being located substantially within the housing in the first configuration; and operating the actuator to adjust the support member from the first configuration to a second configuration, the support member extending through the opening in the housing and into the head of the patient's proximal femur in the second configuration.

16. The method of claim 15, wherein the forming step comprises forming the aperture in the greater trochanter of the patient's proximal femur.

17. The method of claim 15, wherein in the first configuration, the support member is located proximate to the distal end of the housing.

18. The method of claim 15, wherein the operating step comprises pulling the actuator proximally.

\* \* \* \* \*